(12) United States Patent
Ben-Tsur et al.

(10) Patent No.: US 12,115,330 B2
(45) Date of Patent: Oct. 15, 2024

(54) DEVICE AND METHOD FOR DELIVERING AN INGESTIBLE MEDICAMENT INTO THE GASTROINTESTINAL TRACT OF A USER

(71) Applicant: VIBRANT LTD., Yokneam (IL)

(72) Inventors: Lior Ben-Tsur, Netanya (IL); Shai Molnar, Shorashim (IL); Ronny Shabbat, Kibbutz Yizra'el (IL)

(73) Assignee: Vibrant Ltd., Yokneam (IL)

( * ) Notice: Subject to any disclaimer, the term of this patent is extended or adjusted under 35 U.S.C. 154(b) by 643 days.

(21) Appl. No.: 17/419,187

(22) PCT Filed: Jan. 2, 2020

(86) PCT No.: PCT/IB2020/050008
§ 371 (c)(1),
(2) Date: Jun. 30, 2021

(87) PCT Pub. No.: WO2020/141469
PCT Pub. Date: Jul. 9, 2020

(65) Prior Publication Data
US 2022/0111187 A1 Apr. 14, 2022

(30) Foreign Application Priority Data
Jan. 3, 2019 (GB) ..................... 1900082

(51) Int. Cl.
*A61M 31/00* (2006.01)
*A61B 5/00* (2006.01)
(Continued)

(52) U.S. Cl.
CPC ......... *A61M 31/002* (2013.01); *A61B 5/0051* (2013.01); *A61B 5/073* (2013.01);
(Continued)

(58) Field of Classification Search
CPC ........ A61M 31/002; A61M 2210/1042; A61M 31/00
See application file for complete search history.

(56) References Cited

U.S. PATENT DOCUMENTS

| 3,485,235 A | 12/1969 | Felson |
| 4,239,040 A | 12/1980 | Hosoya et al. |

(Continued)

FOREIGN PATENT DOCUMENTS

| CN | 1829466 A | 9/2006 |
| CN | 101810481 A | 8/2010 |

(Continued)

OTHER PUBLICATIONS

'Smart capsule to target colon diseases', Ben Gruber, Sep. 30, 2015, Reuters Health News.

(Continued)

*Primary Examiner* — William R Carpenter
(74) *Attorney, Agent, or Firm* — Momentum IP; Marc Van Dyke

(57) ABSTRACT

Devices and methods for delivering an ingestible medicament of a medicament tablet into the gastrointestinal tract of a user. A device according to the invention includes a vibrating ingestible capsule and a hollow medicament compartment housing. The vibrating capsule includes a housing, a vibrating agitation mechanism disposed within the housing, a power supply, and a control element. The hollow medicament compartment housing is associated with the housing of the capsule and includes at least one aperture. The hollow of the medicament compartment housing is configured to have the medicament tablet disposed therein. The aperture(s) are dimensioned to enable fluid communication the surrounding environment and the hollow.

19 Claims, 10 Drawing Sheets

(51) Int. Cl.
 *A61B 5/07* (2006.01)
 *A61K 9/00* (2006.01)
 *A61M 37/00* (2006.01)

(52) U.S. Cl.
 CPC .............. *A61B 5/42* (2013.01); *A61B 5/4839* (2013.01); *A61B 5/6861* (2013.01); *A61K 9/0053* (2013.01); *A61M 31/00* (2013.01); *A61M 37/00* (2013.01); *A61B 2562/162* (2013.01); *A61M 2205/3306* (2013.01); *A61M 2205/3327* (2013.01); *A61M 2205/3341* (2013.01); *A61M 2205/3344* (2013.01); *A61M 2205/3368* (2013.01); *A61M 2205/8206* (2013.01); *A61M 2210/1053* (2013.01); *A61M 2210/106* (2013.01); *A61M 2210/1064* (2013.01)

(56) References Cited

U.S. PATENT DOCUMENTS

| | | |
|---|---|---|
| 4,507,115 A | 3/1985 | Kambara et al. |
| 5,170,801 A * | 12/1992 | Casper ................. A61B 5/073 604/113 |
| 6,453,199 B1 | 9/2002 | Kobozev |
| 6,632,216 B2 | 10/2003 | Houzego et al. |
| 6,687,537 B2 | 2/2004 | Bernabei |
| 6,776,165 B2 | 8/2004 | Jin |
| 6,929,363 B2 | 8/2005 | Sakai et al. |
| 6,984,205 B2 | 1/2006 | Gazdzinski |
| 7,076,284 B2 | 7/2006 | Segawa et al. |
| 7,354,397 B2 | 4/2008 | Fujita et al. |
| 7,510,537 B2 | 3/2009 | Imboden et al. |
| 7,686,788 B2 | 3/2010 | Freyman et al. |
| 7,797,033 B2 | 9/2010 | DAndrea et al. |
| 7,942,811 B2 | 5/2011 | Segawa et al. |
| 8,021,357 B2 | 9/2011 | Tanaka et al. |
| 8,021,384 B2 | 9/2011 | Weiss et al. |
| 8,036,748 B2 | 10/2011 | Zdeblick et al. |
| 8,038,600 B2 | 10/2011 | Uchiyama et al. |
| 8,147,482 B2 | 4/2012 | Shimizu et al. |
| 8,202,697 B2 | 6/2012 | Holmes |
| 8,216,130 B2 | 7/2012 | Glukhovsky et al. |
| 8,295,932 B2 | 10/2012 | Bitton et al. |
| 8,518,022 B2 | 8/2013 | Trovato et al. |
| 8,597,278 B2 | 12/2013 | Trovato et al. |
| 8,701,677 B2 | 4/2014 | Duan et al. |
| 8,755,888 B2 | 6/2014 | Voznesensky et al. |
| 8,771,730 B2 | 7/2014 | Navon |
| 8,945,005 B2 | 2/2015 | Hafezi et al. |
| 9,078,799 B2 | 7/2015 | Shohat et al. |
| 9,156,169 B2 | 10/2015 | Duan et al. |
| 9,232,909 B2 | 1/2016 | Duan et al. |
| 9,511,211 B2 | 12/2016 | Tange et al. |
| 9,532,923 B2 | 1/2017 | Shohat et al. |
| 9,538,937 B2 | 1/2017 | Rohde et al. |
| 9,550,050 B2 | 1/2017 | Dijksman |
| 9,572,746 B2 | 2/2017 | Asfora |
| 9,707,150 B2 | 7/2017 | Shabbat |
| 9,730,336 B2 | 8/2017 | Arneson et al. |
| 9,750,923 B2 | 9/2017 | Niichel et al. |
| 9,770,588 B2 | 9/2017 | Bettinger |
| 9,919,152 B2 | 3/2018 | Levine et al. |
| 10,118,035 B2 | 11/2018 | Perez et al. |
| 10,172,598 B2 | 1/2019 | Amoako-Tuffour et al. |
| 10,369,463 B2 | 8/2019 | Barney et al. |
| 10,537,720 B2 | 1/2020 | Ben-Tsur |
| 10,543,348 B2 | 1/2020 | Ben-Tsur |
| 10,814,113 B2 | 10/2020 | Ben-Tsur et al. |
| 10,874,339 B2 | 12/2020 | Chavan et al. |
| 10,888,277 B1 | 1/2021 | Ben-Tsur et al. |
| 10,905,378 B1 | 2/2021 | Ben-Tsur et al. |
| 11,020,018 B2 | 6/2021 | Ben-Tsur et al. |
| 11,116,658 B2 | 9/2021 | Ilan |
| 11,351,111 B2 | 6/2022 | Kelrich |
| 2002/0099310 A1 | 7/2002 | Kimchy et al. |
| 2002/0132226 A1 | 9/2002 | Nair et al. |
| 2003/0020810 A1 | 1/2003 | Takizawa et al. |
| 2004/0030454 A1 | 2/2004 | Kim et al. |
| 2004/0253304 A1 | 12/2004 | Gross et al. |
| 2004/0267240 A1 | 12/2004 | Gross et al. |
| 2005/0058701 A1 | 3/2005 | Gross et al. |
| 2005/0085696 A1 | 4/2005 | Uchiyama et al. |
| 2005/0148847 A1 | 7/2005 | Uchiyama et al. |
| 2005/0177069 A1 | 8/2005 | Takizawa et al. |
| 2006/0169293 A1 | 8/2006 | Yokoi et al. |
| 2006/0211963 A1 | 9/2006 | Spirk et al. |
| 2006/0270899 A1 | 11/2006 | Amirana |
| 2006/0276729 A1 | 12/2006 | Reed et al. |
| 2007/0015952 A1 | 1/2007 | Chang et al. |
| 2007/0032699 A1 | 2/2007 | Segawa |
| 2007/0238940 A1 | 10/2007 | Amirana |
| 2008/0051635 A1 * | 2/2008 | Tanaka ..................... A61B 1/06 600/160 |
| 2008/0161639 A1 | 7/2008 | Katayama et al. |
| 2008/0188837 A1 | 8/2008 | Belsky et al. |
| 2008/0269664 A1 | 10/2008 | Trovato et al. |
| 2008/0275430 A1 | 11/2008 | Belsky et al. |
| 2008/0281238 A1 | 11/2008 | Oohashi et al. |
| 2009/0281380 A1 | 11/2009 | Miller et al. |
| 2009/0306633 A1 | 12/2009 | Trovato et al. |
| 2009/0318841 A1 | 12/2009 | Shohat et al. |
| 2010/0049012 A1 | 2/2010 | Dijksman et al. |
| 2010/0217079 A1 | 8/2010 | Tichy |
| 2010/0222670 A1 | 9/2010 | Demierre et al. |
| 2011/0208011 A1 | 8/2011 | Ben-Horin |
| 2011/0319727 A1 | 12/2011 | Ishihara |
| 2013/0158452 A1 | 6/2013 | Juto et al. |
| 2013/0253387 A1 | 9/2013 | Bonutti et al. |
| 2013/0267788 A1 | 10/2013 | Duan et al. |
| 2014/0221741 A1 | 8/2014 | Wang et al. |
| 2015/0011829 A1 | 1/2015 | Wang et al. |
| 2015/0018614 A1 | 1/2015 | Duan et al. |
| 2015/0018615 A1 | 1/2015 | Duan et al. |
| 2015/0065926 A1 | 3/2015 | Nakamura et al. |
| 2015/0073315 A1 | 3/2015 | Shabbat |
| 2015/0223727 A1 | 8/2015 | Kimchy et al. |
| 2015/0313792 A1 | 11/2015 | Shohat et al. |
| 2015/0380140 A1 | 12/2015 | Duan et al. |
| 2016/0183878 A1 | 6/2016 | Weast et al. |
| 2016/0287058 A1 | 10/2016 | Ye et al. |
| 2016/0303133 A1 | 10/2016 | Dudley et al. |
| 2016/0310357 A1 | 10/2016 | Duan et al. |
| 2017/0020374 A1 | 1/2017 | Duan et al. |
| 2017/0035407 A1 | 2/2017 | Duan et al. |
| 2017/0035520 A1 | 2/2017 | Duan et al. |
| 2017/0135897 A1 | 5/2017 | Shohat et al. |
| 2017/0273863 A1 | 9/2017 | Shabbat |
| 2017/0296425 A1 | 10/2017 | Duan et al. |
| 2017/0296428 A1 | 10/2017 | Duan et al. |
| 2017/0340242 A1 | 11/2017 | Duan |
| 2018/0055597 A1 | 3/2018 | Duan et al. |
| 2018/0070857 A1 | 3/2018 | Jones |
| 2018/0084975 A1 | 3/2018 | Duan et al. |
| 2018/0168490 A1 | 6/2018 | Jones et al. |
| 2019/0224070 A1 | 7/2019 | Ben-Tsur et al. |
| 2019/0307999 A1 | 10/2019 | Ben-Tsur |
| 2019/0308002 A1 | 10/2019 | Ben-Tsur |
| 2020/0214592 A1 | 7/2020 | Ben-Tsur et al. |
| 2020/0229733 A1 | 7/2020 | Tzur et al. |
| 2020/0246216 A1 | 8/2020 | Molnar |
| 2020/0315541 A1 | 10/2020 | Ben-Tsur et al. |
| 2021/0023357 A1 | 1/2021 | Ben-Tsur |
| 2021/0066998 A1 | 3/2021 | Molnar |
| 2021/0196296 A1 | 7/2021 | Ben-Tsur et al. |
| 2021/0236381 A1 | 8/2021 | Ben-Tsur et al. |
| 2021/0290483 A1 | 9/2021 | Molnar et al. |
| 2021/0322741 A1 | 10/2021 | Ben-Tsur et al. |
| 2021/0386316 A1 | 12/2021 | Ben-Tsur et al. |
| 2022/0054352 A1 | 2/2022 | Shohat et al. |

(56) References Cited

U.S. PATENT DOCUMENTS

FOREIGN PATENT DOCUMENTS

| | | |
|---|---|---|
| CN | 102743174 A | 10/2012 |
| CN | 102743175 A | 10/2012 |
| CN | 102743176 A | 10/2012 |
| CN | 202483565 U | 10/2012 |
| CN | 102813515 A | 12/2012 |
| CN | 102860810 A | 1/2013 |
| CN | 202699138 U | 1/2013 |
| CN | 202821355 U | 3/2013 |
| CN | 202843564 U | 4/2013 |
| CN | 202843608 U | 4/2013 |
| CN | 202875332 U | 4/2013 |
| CN | 103222842 A | 7/2013 |
| CN | 203634116 U | 6/2014 |
| CN | 104898850 A | 9/2015 |
| CN | 105025245 A | 11/2015 |
| CN | 105079970 A | 11/2015 |
| CN | 105380777 A | 3/2016 |
| CN | 105411505 A | 3/2016 |
| CN | 205108749 U | 3/2016 |
| CN | 205286889 U | 3/2016 |
| CN | 105939451 A | 9/2016 |
| CN | 105942959 A | 9/2016 |
| CN | 105996961 A | 10/2016 |
| CN | 106056588 A | 10/2016 |
| CN | 106097335 A | 11/2016 |
| CN | 106137760 A | 11/2016 |
| CN | 106204599 A | 12/2016 |
| CN | 205758500 U | 12/2016 |
| CN | 106373137 A | 2/2017 |
| CN | 205913317 U | 2/2017 |
| CN | 205928774 U | 2/2017 |
| CN | 106923787 A | 7/2017 |
| CN | 106934799 A | 7/2017 |
| CN | 107174188 A | 9/2017 |
| CN | 107233580 A | 10/2017 |
| CN | 107240091 A | 10/2017 |
| CN | 107375951 A | 11/2017 |
| EP | 2987447 A1 | 2/2016 |
| EP | 2995240 A1 | 3/2016 |
| JP | 2001062397 A | 3/2001 |
| JP | 2002163359 A | 6/2002 |
| JP | 2005052502 A | 3/2005 |
| JP | 2010503451 A | 2/2010 |
| JP | 2010246703 A | 11/2010 |
| JP | 2013535756 A | 9/2013 |
| WO | 2006025013 A1 | 3/2006 |
| WO | 2007013059 A2 | 2/2007 |
| WO | 2008012700 A1 | 1/2008 |
| WO | 2008035329 A2 | 3/2008 |
| WO | 2009063375 A1 | 5/2009 |
| WO | 2009/153973 A1 | 12/2009 |
| WO | 2013121276 A1 | 8/2013 |
| WO | 2018055487 A1 | 3/2018 |

OTHER PUBLICATIONS

'Advanced Delivery Devices—IntelliCap: An Intelligent, Electronic Capsule for Oral Drug Delivery & Development', Drug Development & Delivery, Apr. 2013.
Machine Translation (by Google Patents) for CN 102743174 published on Oct. 24, 2012.
Machine Translation (by Google Patents) for CN 102743175 published on Oct. 24, 2012.
Machine Translation (by Google Patents) for CN 102743176 published on Oct. 24, 2012.
Machine Translation (by Google Patents) for CN 102813515 published on Dec. 12, 2012.
Machine Translation (by Google Patents) for CN 102860810 published on Jan. 9, 2013.
Machine Translation (by Google Patents) for CN 03222842 published on Jul. 31, 2013.
Machine Translation (by Google Patents) for CN 104898850 published on Sep. 9, 2015.
Machine Translation (by Google Patents) for CN 105025245 published on Nov. 4, 2015.
Machine Translation (by Google Patents) for CN 105079970 published on Nov. 25, 2015.
Machine Translation (by Google Patents) for CN 105411505 published on Mar. 23, 2016.
Machine Translation (by Google Patents) for CN 105939451 published on Sep. 14, 2016.
Machine Translation (by Google Patents) for CN 105942959 published on Sep. 21, 2016.
Machine Translation (by Google Patents) for CN 105996961 published on Oct. 12, 2016.
Machine Translation (by Google Patents) for CN 106056588 published on Oct. 26, 2016.
Machine Translation (by Google Patents) for CN 106097335 published on Nov. 9, 2016.
Machine Translation (by Google Patents) for CN 106137760 published on Nov. 23, 2016.
Machine Translation (by Google Patents) for CN 106204599 published on Dec. 7, 2016.
Machine Translation (by Google Patents) for CN 106373137 published on Feb. 1, 2017.
Machine Translation (by Google Patents) for CN 106923787 published on Jul. 7, 2017.
Machine Translation (by Google Patents) for CN 106934799 published on Jul. 7, 2017.
Machine Translation (by Google Patents) for CN 107174188 published on Sep. 19, 2017.
Machine Translation (by Google Patents) for CN 107233580 published on Oct. 10, 2017.
Machine Translation (by Google Patents) for CN 107240091 published on Oct. 10, 2017.
Machine Translation (by Google Patents) for CN 107375951 published on Nov. 24, 2017.
Machine Translation (by Google Patents) for CN 1829466 published on Sep. 6, 2006.
Machine Translation (by Google Patents) for CN 202483565 published on Oct. 10, 2012.
Machine Translation (by Google Patents) for CN 202699138 published on Jan. 30, 2013.
Machine Translation (by Google Patents) for CN 202821355 published on Mar. 27, 2013.
Machine Translation (by Google Patents) for CN 202843564 published on Apr. 3, 2013.
Machine Translation (by Google Patents) for CN 202843608 published on Apr. 3, 2013.
Machine Translation (by Google Patents) for CN 202875332 published on Apr. 17, 2013.
Machine Translation (by Google Patents) for CN 203634116 published on Jun. 11, 2014.
Machine Translation (by Google Patents) for CN 205108749 published on Mar. 30, 2016.
Machine Translation (by Google Patents) for CN 205758500 published on Dec. 7, 2016.
Machine Translation (by Google Patents) for CN 205913317 published on Feb. 1, 2017.
Machine Translation (by Google Patents) for CN 205928774 published on Feb. 8, 2017.
Machine Translation (by Google Patents) for JP 2001062397 published on Mar. 13, 2001.
Machine Translation (by Google Patents) for JP 2010503451 published on Feb. 4, 2010.
Co-pending U.S. Appl. No. 15/882,283, filed Jan. 29, 2018.
Co-pending U.S. Appl. No. 16/403,553, filed May 5, 2019.
Abandoned U.S. Appl. No. 15/882,552, filed Jan. 29, 2018.
Co-pending U.S. Appl. No. 16/823,035, filed Mar. 18, 2020.
Co-pending U.S. Appl. No. 16/377,213, filed Apr. 7, 2019.
Co-pending U.S. Appl. No. 17/038,226, filed Sep. 30, 2020.
Machine Translation (by Google Patents) for CN 101810481 published on Aug. 25, 2010.

(56) References Cited

OTHER PUBLICATIONS

Machine Translation (by Google Patents) for CN 105380777 published on Mar. 9, 2016.
Machine Translation (by Google Patents) for CN 205286889 published on Mar. 9, 2016.
Machine Translation (by Google Patents) for JP 2002163359 published on Jun. 7, 2002.
Machine Translation (by Google Patents) for JP 2005052502 published on Mar. 3, 2005.
Machine Translation (by Google Patents) for JP 2010246703 published on Nov. 4, 2010.
Machine Translation (by Google Patents) for JP 2013535756 published on Sep. 12, 2013.

* cited by examiner

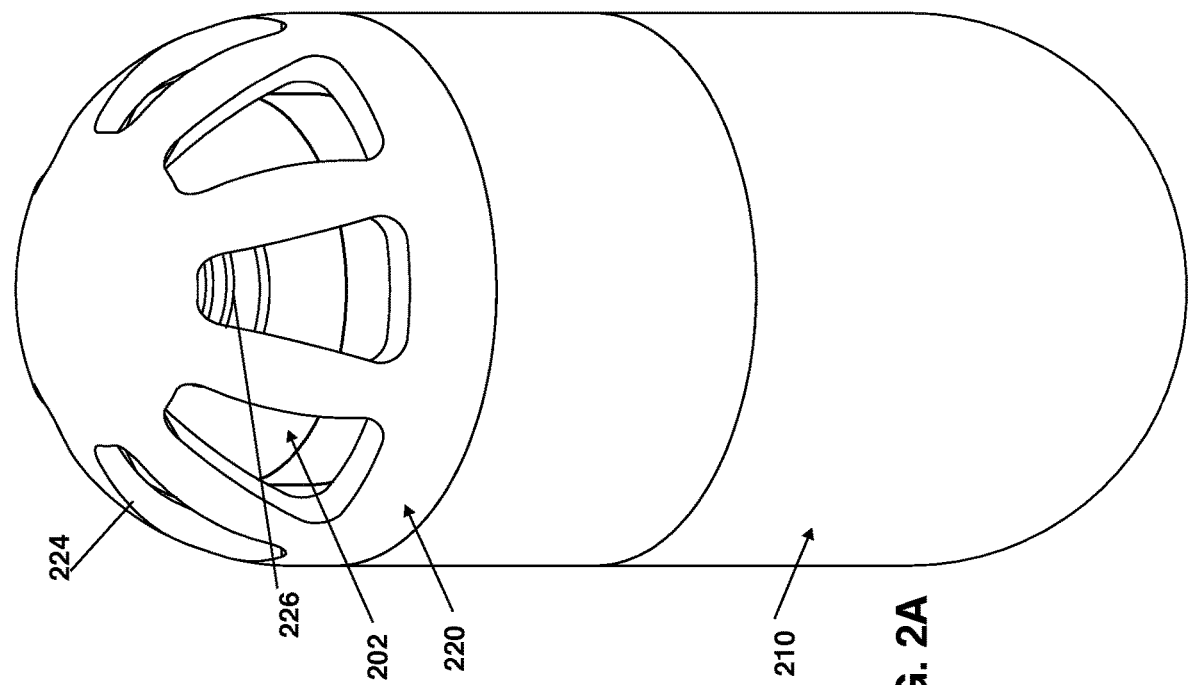
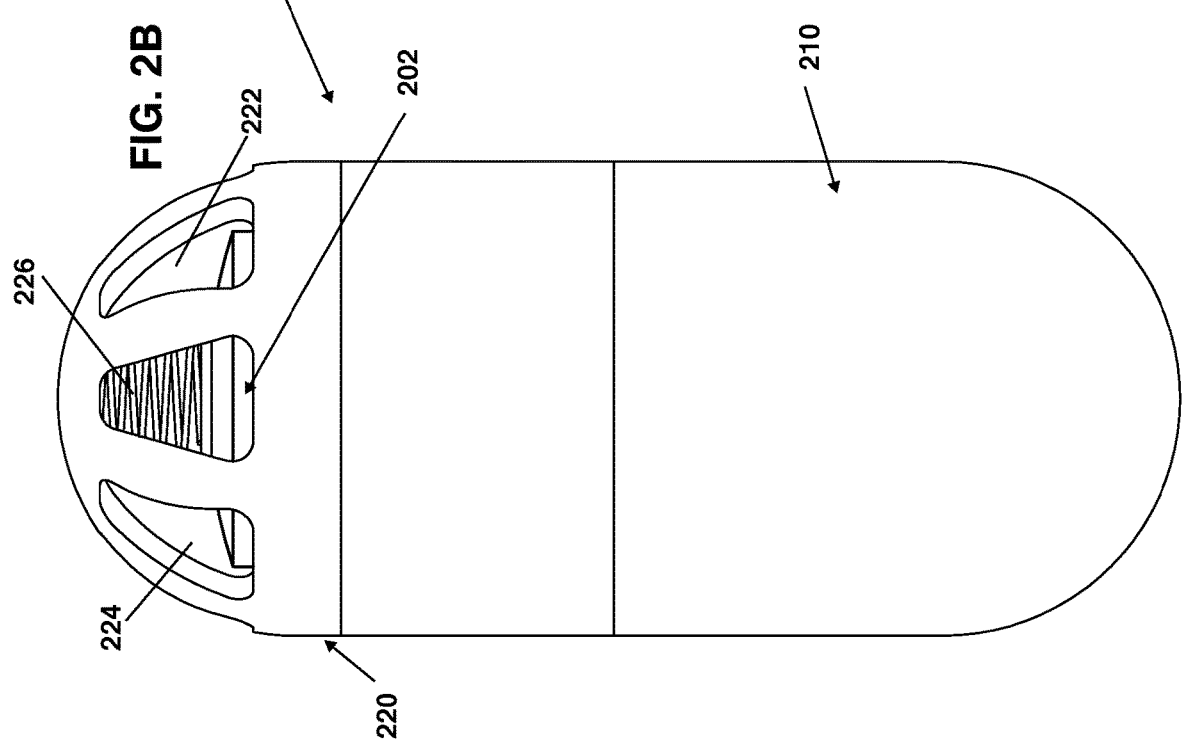

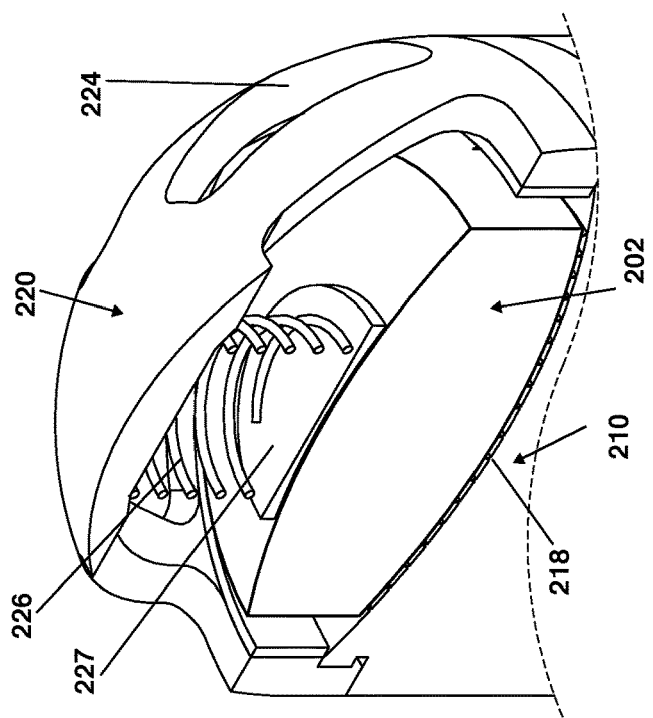
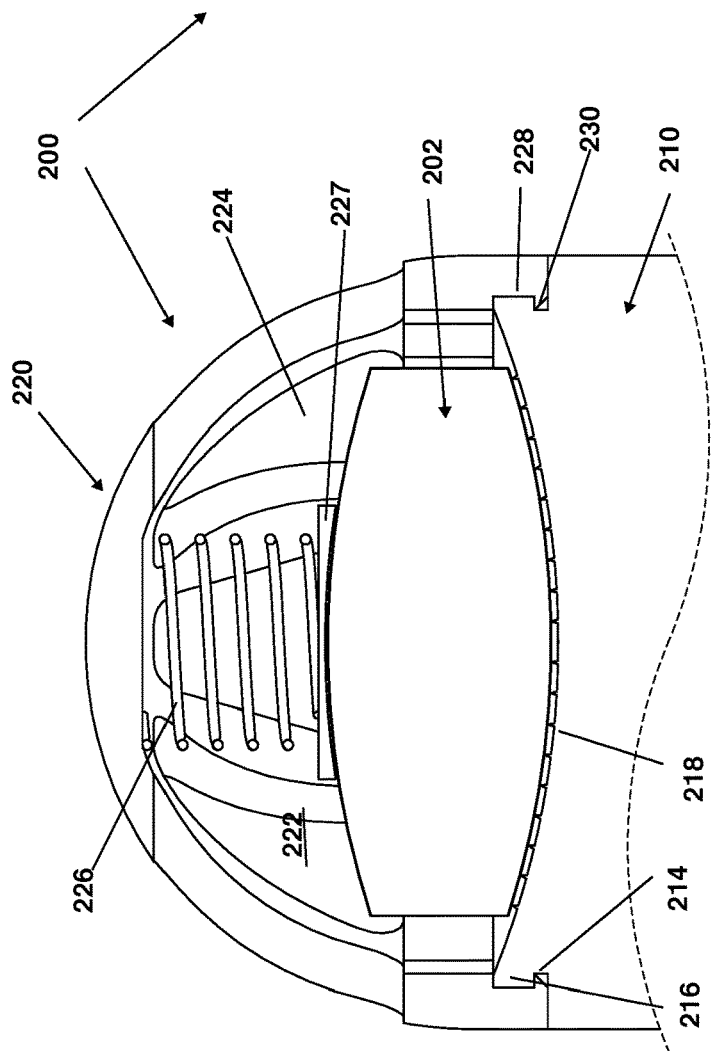
FIG. 3B
FIG. 4B

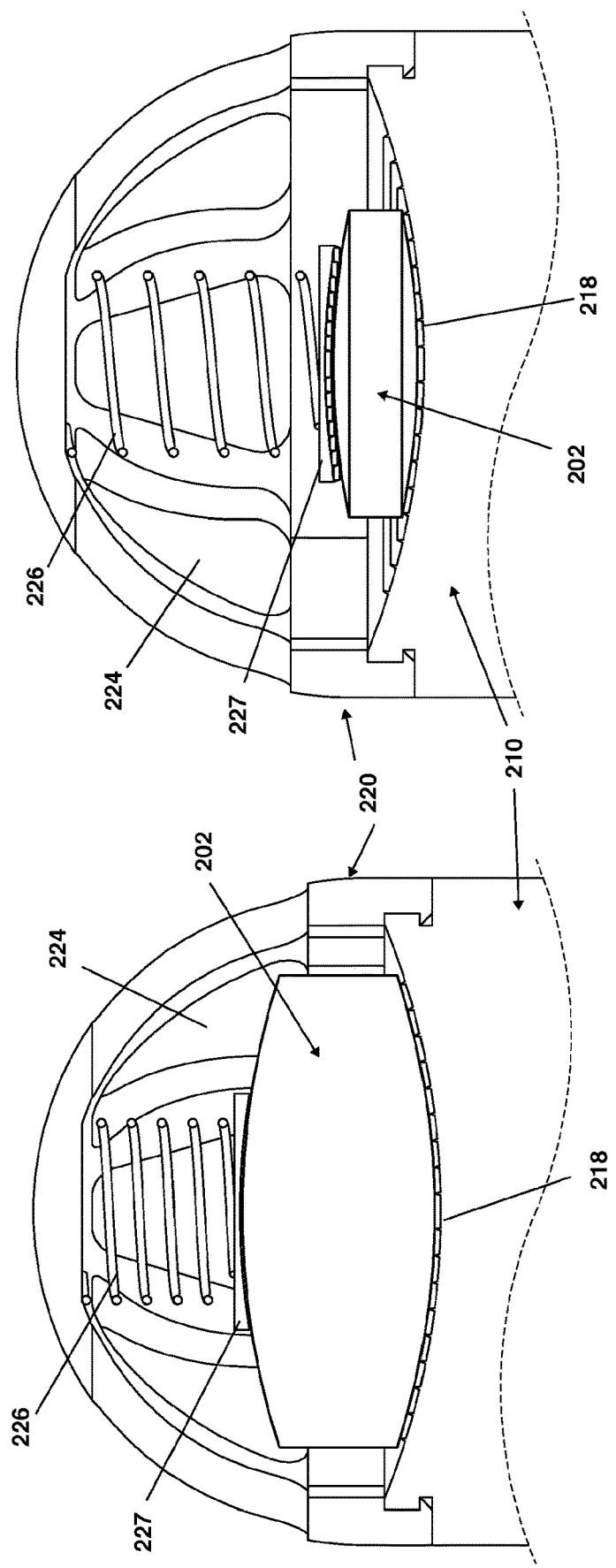

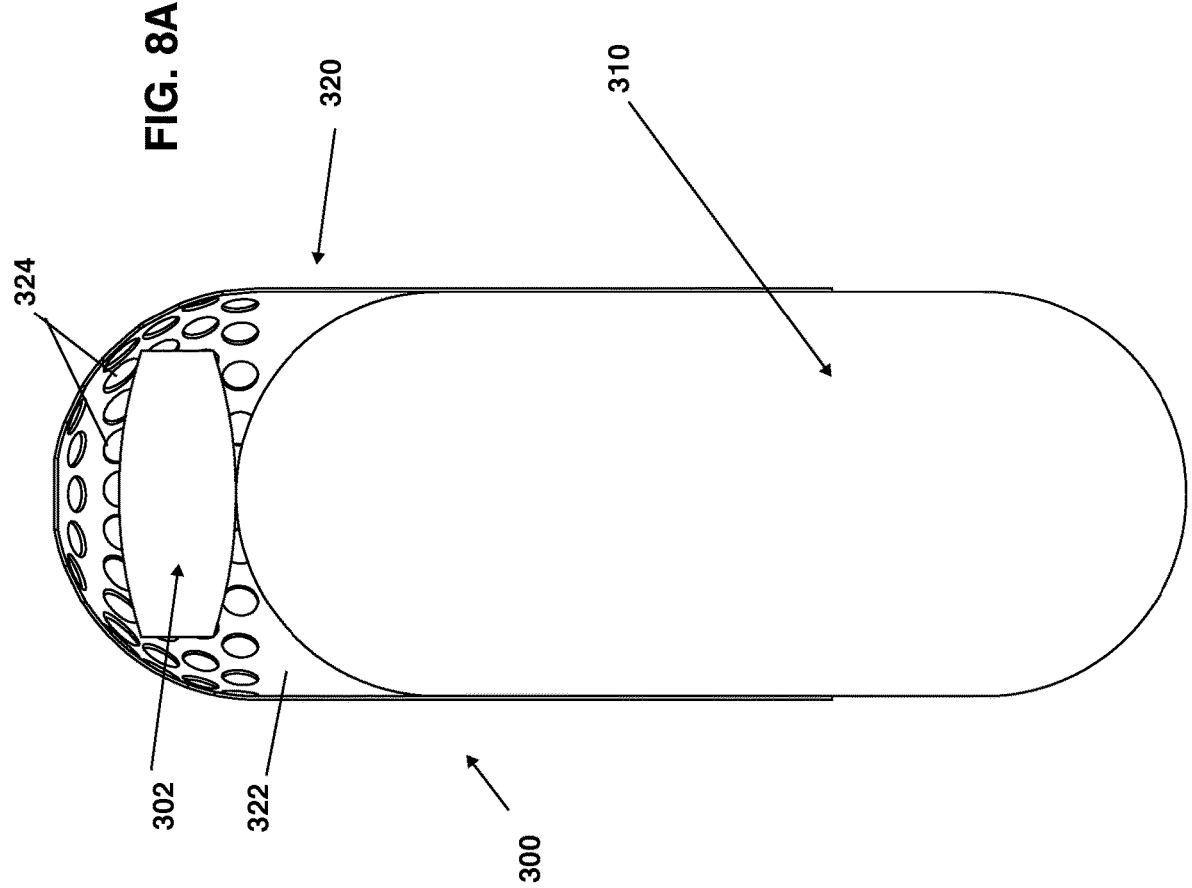

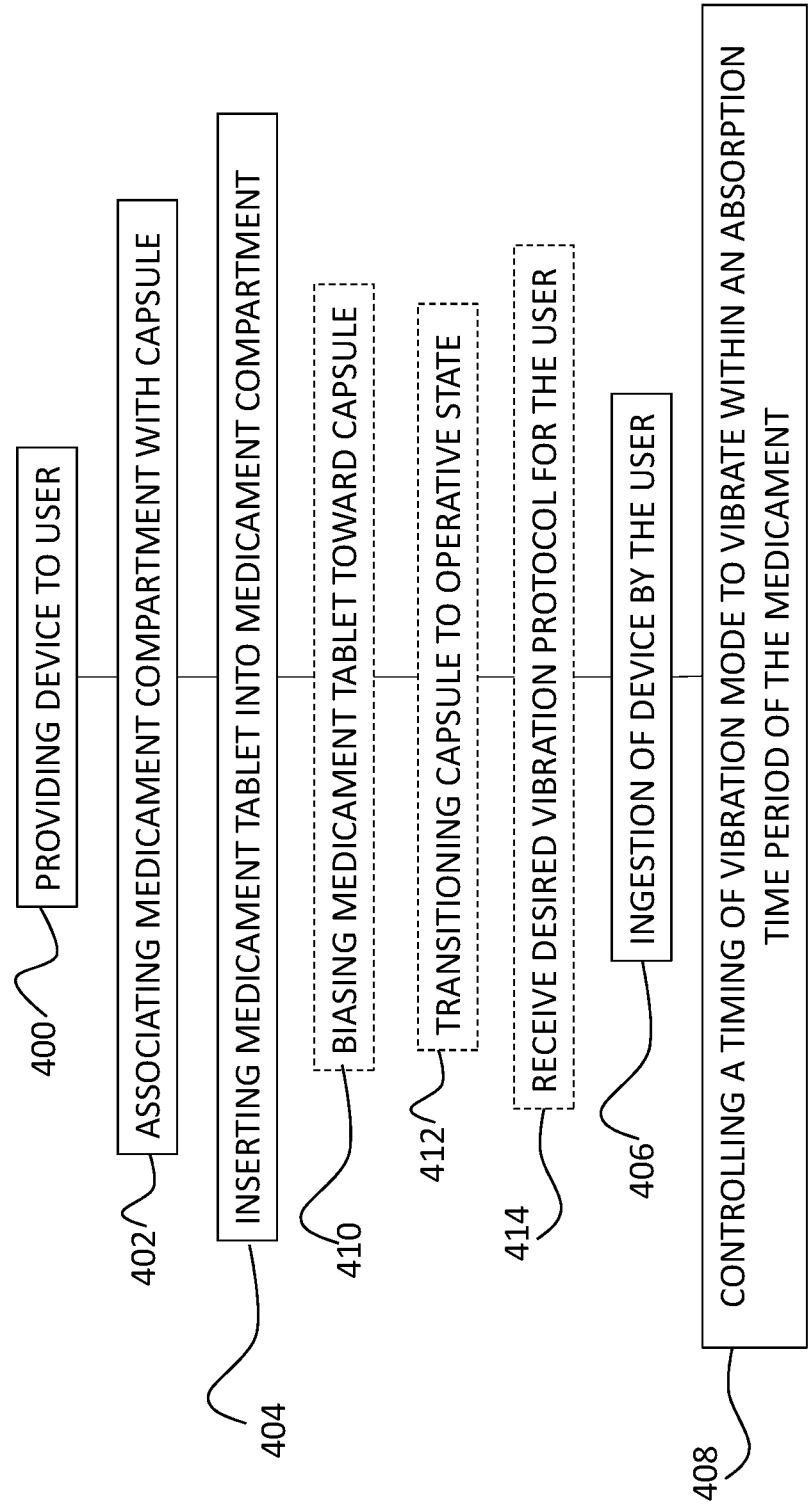

DEVICE AND METHOD FOR DELIVERING AN INGESTIBLE MEDICAMENT INTO THE GASTROINTESTINAL TRACT OF A USER

RELATED APPLICATIONS

The present application gains priority from GB Patent Application Number 1900082.7 filed Jan. 3, 2019 and entitled DEVICE AND METHOD FOR DELIVERING AN INGESTIBLE MEDICAMENT INTO THE GASTROINTESTINAL TRACT OF A USER.

FIELD OF THE INVENTION

The present invention relates in general to devices and methods for delivery of an ingestible medicament into the body of a user, and specifically to devices and methods for such delivery of an ingestible medicament which include a vibrating capsule.

SUMMARY OF THE INVENTION

In accordance with an embodiment of the present invention, there is provided a device for delivering an ingestible medicament of a medicament tablet into the gastrointestinal tract of a user, the device including:
  a vibrating ingestible capsule including:
  a housing;
  a vibrating agitation mechanism disposed within the housing and adapted such that, in a vibration mode of operation, the housing exerts vibrations on an environment surrounding the vibrating gastrointestinal capsule;
  a power supply disposed within the housing and adapted to power the vibrating agitation mechanism; and
  a control element adapted to activate the vibrating agitation mechanism to be operative in the vibration mode of operation; and
  a hollow medicament compartment housing, associated with the housing, and having at least one aperture formed in the medicament compartment housing,
  wherein a hollow of the medicament compartment housing is dimensioned and configured to have the medicament tablet disposed therein, and
  wherein the at least one aperture is dimensioned and configured to enable fluid communication between an environment surrounding the medicament compartment housing and the hollow.

In accordance with an embodiment of the present invention, there is provided a method of delivering an ingestible medicament into a gastrointestinal tract of a user, the method including:
  providing to the user the device as described hereinabove, for ingestion by the user;
  following the user ingesting the device, controlling the vibrating ingestible capsule such that the vibration mode of operation at least partially transpires within at least one of an estimated absorption time period and an actual absorption time period of the ingestible medicament within the gastrointestinal tract of the user.

In accordance with an embodiment of the present invention, there is provided a method of delivering an ingestible medicament into a gastrointestinal tract of a user, the method including:
  providing to the user the device as described herein;
  inserting into the hollow of the medicament compartment housing the medicament tablet; and
  following the user ingesting the device having the medicament tablet disposed in the hollow, controlling the vibrating ingestible capsule such that the vibration mode of operation at least partially transpires within at least one of an estimated absorption time period and an actual absorption time period of the ingestible medicament within the gastrointestinal tract of the user.

In accordance with an embodiment of the present invention, there is provided a hollow medicament delivery compartment adapted to be associated with a vibrating ingestible capsule for delivery of an ingestible medicament of a medicament tablet into the gastrointestinal tract of a user, the hollow medicament delivery compartment being dimensioned and configured to have the medicament tablet disposed therein, and including at least one aperture formed in the hollow medicament delivery compartment,
  wherein the at least one aperture is dimensioned and configured to enable fluid communication between an environment surrounding the hollow medicament delivery compartment.

In accordance with an embodiment of the present invention, there is provided a vibrating ingestible capsule adapted to be associated with a hollow medicament delivery compartment for delivering an ingestible medicament of a medicament tablet into the gastrointestinal tract of a user, the vibrating ingestible capsule including:
  a housing including an attachment mechanism adapted for mutual attachment to a corresponding attachment mechanism of the hollow medicament delivery compartment;
  a vibrating agitation mechanism disposed within the housing and adapted such that, in a vibration mode of operation, the housing exerts vibrations on an environment surrounding the vibrating gastrointestinal capsule;
  a power supply disposed within the housing and adapted to power the vibrating agitation mechanism; and
  a control element adapted to activate the vibrating agitation mechanism to be operative in the vibration mode of operation,
  wherein at least one vibration parameter of the vibrating agitation mechanism is set so as to promote absorption of the ingestible medicament into the bloodstream of the user.

In accordance with an embodiment of the present invention, there is provided a method for delivering an ingestible medicament of a medicament tablet into the gastrointestinal tract of a user, the method including:
  providing a vibrating ingestible capsule including:
  a housing;
  a vibrating agitation mechanism disposed within the housing and adapted such that, in a vibration mode of operation, the housing exerts vibrations on an environment surrounding the vibrating gastrointestinal capsule;
  a power supply disposed within the housing and adapted to power the vibrating agitation mechanism; and
  a control element adapted to activate the vibrating agitation mechanism to be operative in the vibration mode of operation; and
  associating a hollow medicament compartment housing with the housing, the hollow medicament compartment having at least one aperture formed therein;
  inserting the medicament tablet into the hollow medicament compartment housing;
  ingesting an assembly of the vibrating ingestible capsule, the hollow medicament compartment housing, and the medicament tablet by the user; and
  following the user ingesting the assembly, controlling the vibrating ingestible capsule such that the vibration mode of operation at least partially transpires within at least one of an estimated absorption time period and an actual absorption time period of the ingestible medicament within the gastrointestinal tract of the user.

BRIEF DESCRIPTION OF THE FIGURES

The foregoing discussion will be understood more readily from the following detailed description of the invention, when taken in conjunction with the accompanying FIGS. 1-9), in which:

FIGS. 2A and 2B are, respectively, a perspective view illustration and a planar side view illustration of a first embodiment of a device for delivering an ingestible medicament into the gastrointestinal tract of a user, the device having a medicament tablet including the ingestible medicament disposed therein, according to an embodiment of the present invention;

FIGS. 3A and 3B are, respectively, a complete and a partial perspective sectional illustration of the device of FIG. 2, having the medicament tablet disposed therein;

FIGS. 4A and 4B are, respectively, a complete and a partial planar sectional illustration of the device of FIG. 2, having the medicament tablet disposed therein;

FIGS. 5A and 5B are, respectively, partial sectional illustrations of the device of FIG. 2, at two times during use thereof;

FIGS. 8A and 8B are, respectively, a complete and a partial planar sectional illustration of the device of FIGS. 7A and 7B, having the medicament tablet disposed therein; and FIG. 9 is a schematic flowchart of a method for delivering an ingestible medicament of a medicament tablet into the gastrointestinal tract of user according to the present invention, the method being based on use of any one of the devices of FIGS. 1 to 8B.

DESCRIPTION OF THE PREFERRED EMBODIMENTS

Figure 1:
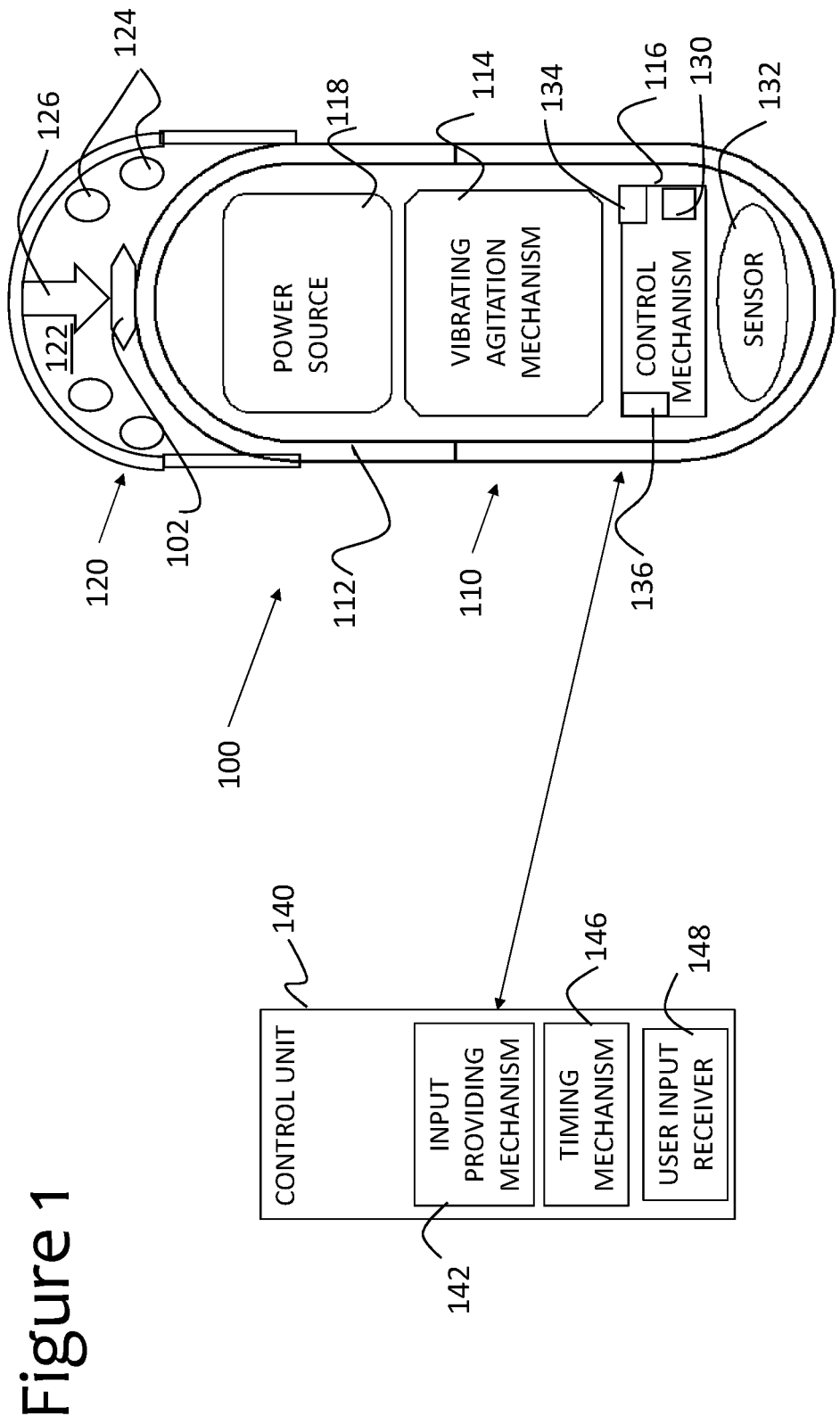
FIG. 1 is a schematic block diagram of a device for delivering an ingestible medicament into the gastrointestinal tract of a user according to an embodiment of the present invention.

The principles of the inventive devices and methods for delivery of an ingestible medicament into the body of a user, and specifically to devices and methods for such delivery of an ingestible medicament which include a vibrating capsule, may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

For the purpose of this application, the term "user" relates to a human.

For the purpose of this application, the term "vibrating ingestible capsule" relates to an ingestible capsule adapted to at least intermittently vibrate, for a cumulative duration of at least one minute, in accordance with a vibration protocol of the capsule.

For the purpose of this application, the term "vibrating agitation mechanism" refers to any type of mechanism that vibrates or causes elements in its vicinity to vibrate, including a motor driven agitator such as a motor driven eccentric weight or a motor driven pendulum.

For the purpose of this application, the term "intermittently activated vibrating agitation mechanism" refers to a vibration agitation mechanism that vibrates or causes elements in its vicinity to vibrate and is operative at certain times, and does not vibrate or cause elements in its vicinity to vibrate at other times, the activation times being selected by a control element or other control unit controlling the vibration agitation mechanism.

For the purpose of this application, the term "control element", and the equivalent term "controller" refer to a component for controlling operation of mechanical and/or electrical components of the capsule, which includes a processing unit functionally associated with a non-volatile computer readable storage medium. The storage medium stores instructions, which, when executed by the processing unit, cause the processing unit to carry out actions which control the operation of the mechanical and/or electrical components of the capsule. For example, the instructions may include instructions to activate operation of a vibrating agitation mechanism at a specific time, frequency, cycle, and/or for a specific duration. The control element may be functionally associated with, or may include, a transceiver for receiving input, which input may be used to trigger execution of specific instructions stored in the storage medium.

For the purpose of this application, the term "biasing mechanism" refers to any structure, or device, adapted to apply continuous pressure to a second element, even when the position of the second element changes relative to an anchoring point of the structure or device. Biasing mechanisms include springs, such as compression springs, spring loaded and/or flexible leaves, plungers, and the like.

For the purpose of this application, the term "vibration protocol" relates to a protocol specifying vibration parameters of an intermittently activated vibrating agitation mechanism of a vibrating ingestible capsule. Typically, the vibration protocol relates to an activation delay for initiating vibration (e.g., a duration between "initial" activation of the capsule and the first activation of the vibration agitation mechanism), a vibration rate (number of vibration cycles per hour), a vibration duration and a repose duration for each vibration cycle, a vibration frequency, an amount of force exerted by the vibrations, and the like.

For the purpose of this application, the term "treatment procedure" relates to parameters of a treatment utilizing vibrating ingestible capsules, which are typically defined by a treating physician or medical practitioner. For example, the treatment procedure may include the number of capsules to be taken within a specific time duration (e.g., 3 capsules per week, 2 capsules per day), the frequency at which capsules should be taken, the time of day at which capsules should be taken, whether the capsule should be taken with or without food, and the like.

For the purpose of this application, the term "treatment protocol" relates to all aspects of treatment of a user with a vibrating ingestible capsule, and includes the treatment procedure as well as the vibration protocol to be used for treating the user.

For the purpose of this application, the term "activation input" relates to an input received by a control element or control element of a vibrating ingestible capsule, which causes the control element or control element of the capsule to activate itself, so as to be able to process inputs and/or to control additional components of the capsule. The activation input may be received from an element forming part of the capsule, such as a sensor sensing specific conditions in which the capsule should be activated, or from a remote source, such as a remote control element, for example by way of a signal transmitted to the capsule, magnetic field applied to the capsule, specific motion applied to the capsule, or any other type of input provided to the capsule from a remote source.

For the purpose of this application, a vibrating ingestible capsule is said to be in an "inoperative state" when the capsule is in a storage condition, intended to preserve the life of a battery thereof. In the inoperative state, components of the capsule which are intended to receive or to provide an activation input, such as specific sensors, transceivers, and/or timing mechanisms may be active at least to a minimal degree. However, in the inoperative state, no vibration takes place, and a control element controlling vibration of the capsule is inactive.

For the purpose of this application, a vibrating ingestible capsule is said to be in an "operative state" when the control element of the capsule is processing inputs and data, and can cause a vibrating agitation mechanism of the capsule to vibrate or cause elements in its vicinity to vibrate.

For the purpose of this application, an "ingestible medicament" is at least partially absorbable to the bloodstream from within the stomach, small intestine, and large intestine, and more typically, within the stomach or small intestine.

For the purpose of this application, the term "partially absorbable" is meant to include the possibility that the environment within the gastrointestinal tract (including acids, enzymes, etc. thereof) may chemically modify the ingested medicament in order to achieve the characteristic "partially absorbable".

For the purpose of this application, the term "medicament tablet" relates to any dosage form of an ingestible medicament, in which the ingestible medicament maintains a predefined closed contour. This may include a pill, a tablet, a capsule, a liquid-gel capsule, or compressed powder.

For the purpose of this application, the disclosure of a commercial name of a material or drug is meant to be a disclosure of the corresponding generic material or drug, and of the active ingredient(s) within the commercial material or drug and/or within the corresponding generic material or drug.

For the purpose of this application, an estimated absorption time may be determined as follows:

(i) ingestible medicaments that are absorbed in the stomach have an estimated absorption time within a range of 0.5 to 1.5 hours from the time of ingestion of the ingestible medicament;

(ii) ingestible medicaments that are absorbed in the small intestine have an estimated absorption time within a range of 1.0 to 5 hours from the time of ingestion of the ingestible medicament;

(iii) ingestible medicaments that are absorbed in both the stomach and the small intestine have an estimated absorption time within a range of 0.5 to 5 hours from the time of ingestion of the ingestible medicament;

(iv) ingestible medicaments that are absorbed in the large intestine have an estimated absorption time of at least 4 hours, and more typically, within a range of 4 to 30 hours, 6 to 30 hours, 6 to 20 hours, or 8 to 20 hours from the time of ingestion of the ingestible medicament.

The location within the GI tract at which the particular ingestible medicament is absorbed to the bloodstream may often be public knowledge. This location may be provided by, or known to, the manufacturer and/or distributor of the particular ingestible medicament. Alternatively or additionally, the location may be known to relevant medical practitioners, including doctors and pharmacists, and more particularly, to a medical practitioner of the user.

For the purpose of this application, an actual absorption time may be determined from clinical data, in vivo or in vitro, according to accepted clinical procedures known to those of skill in the art. Since actual absorption is achieved over a period of time, the "actual absorption time" or "actual absorption time period" may be defined by the time period at which between 20% and 80% of the absorption occurs. In the absence of such data, the "actual absorption time" or "actual absorption time period" may be defined by determining the "peak" actual absorption time, and building a time period of up to 1 hour on each side of the peak time.

For the purpose of this application, the term "Parkinsonism" is meant to include Parkinson's disease, or symptoms of neurodegeneration associated therewith.

For the purpose of this application, the term "Parkinsonism" is meant to include progressive supranuclear palsy, or symptoms of neurodegeneration associated therewith.

For the purpose of this application, the term "Parkinsonism" is meant to include corticobasal degeneration, or symptoms of neurodegeneration associated therewith.

For the purpose of this application, the term "Parkinsonism" is meant to include multiple system atrophy, or symptoms of neurodegeneration associated therewith.

For the purpose of this application, the term "Parkinsonism" is meant to include Parkinson-plus syndromes (also known as disorders of multiple system degeneration), or symptoms of neurodegeneration associated therewith.

For the purpose of this application, the term "Parkinsonism" is meant to include any neurodegenerative disease in which the subject exhibits at least one (and typically at least two or three) of the classical features of Parkinson's disease: tremor, postural instability, and akinesia or bradykesia.

For the purpose of this application, the term "Parkinsonism" is meant to include any neurodegenerative disease in which the subject positively responds to a dopaminergic treatment.

For the purpose of this application, the term "Parkinsonism" is meant to include any neurodegenerative disease in which the particular subject positively responds to an anticholinergic treatment.

For the purpose of this application, the term "Parkinsonism" is meant to include any neurodegenerative disease in which a dopaminergic treatment is clinically utilized to treat the sufferers or subjects.

For the purpose of this application, the term "Parkinsonism" is meant to include any neurodegenerative disease in which an anticholinergic treatment is clinically utilized to treat the sufferers or subjects.

For the purpose of this application, the term "Parkinson's disease" (PD) is meant as used by those of skill in the art of neurodegenerative diseases. It is believed that PD is due to the loss of brain cells that produce dopamine. Early signs and symptoms of Parkinson's disease include at least one of tremors (or trembling), slowness of movement, body rigidity and stiffness, and gait problems.

For the purpose of this application, the term "treatment of Parkinsonism" and the like refers to at least one of: (i) delaying onset of Parkinsonism (e.g., PD); (ii) mitigating the development of Parkinsonism (e.g., PD); and (iii) managing a condition of Parkinsonism (e.g., PD).

For the purpose of this application, the term "ailment of the GI tract" is meant to include chronic or acute constipation, or symptoms associated therewith.

For the purpose of this application, the term "ailment of the GI tract" is meant to include gastroparesis, or symptoms associated therewith.

For the purpose of this application, the term "ailment of the GI tract" is meant to include Crohn's disease, or symptoms associated therewith.

For the purpose of this application, the term "ailment of the GI tract" is meant to include chronic or acute diarrhea, or symptoms associated therewith.

For the purpose of this application, the term "ailment of the GI tract" is meant to include colitis, or symptoms associated therewith.

For the purpose of this application, the term "ailment of the GI tract" is meant to include dyspepsia or dysphagia, or symptoms associated therewith.

For the purpose of this application, the term "ailment of the GI tract" is meant to include Hirschsprung's disease, or symptoms associated therewith.

For the purpose of this application, the term "ailment of the GI tract" is meant to include irritable bowel syndrome, or symptoms associated therewith.

For the purpose of this application, the term "ailment of the GI tract" is meant to include any disease in which the subject positively responds to an osmotic gastrointestinal treatment.

For the purpose of this application, the term "ailment of the GI tract" is meant to include any disease in which the particular subject positively responds to a stool softening treatment.

For the purpose of this application, the term "ailment of the GI tract" is meant to include any disease in which the particular subject positively responds to a GI contraction inducing treatment.

For the purpose of this application, the term "ailment of the GI tract" is meant to include any disease in which the subject positively responds to a GI fluid absorption inducing treatment.

For the purpose of this application, the term "managing a condition of", with respect to an ailment of the GI tract, is meant to include, inter alia, improving absorption of a medicament, such as a medicament used in the treatment of the ailment of the GI tract (e.g., Linaclotide (Linzess®)), into the bloodstream. Such condition management may be manifested by at least one of (i) improved medicament efficacy due to the increased absorption; and (ii) reduced dosage of the medicament, due to the increased medicament absorption efficacy.

For the purpose of this application, the term "managing a condition of", with respect to Parkinsonism and the like, is meant to include, inter alia, improving absorption of a medicament, such as a medicament used in the treatment of Parkinsonism (e.g., levodopa), into the bloodstream. Such condition management may be manifested by at least one of (i) improved medicament efficacy due to the increased absorption; and (ii) reduced dosage of the medicament, due to the increased medicament absorption efficacy.

For the purpose of this application, a first element is said to envelop a second element, if the second element is disposed within the first element, and the first element fully surrounds the second element. The second element need not be attached to the first element, and may be movable relative to the first element, within the first element, but may also be attached to the first element.

For the purpose of this application, a first element is said to partially envelop a second element, if at least part of the exterior surface of the second element is covered by the first element or is surrounded by the first element. The second element need not be attached to the first element, and may be movable relative to the first element, within the first element, but may also be attached to the first element.

Referring now to the drawings, FIG. 1 is a schematic block diagram of a device 100 for delivering an ingestible medicament within a medicament tablet 102 into the gastrointestinal tract of a user according to an embodiment of the present invention.

As seen in FIG. 1, device 100 includes vibrating ingestible capsule 110. Capsule 110 includes a capsule housing or shell 112, arranged along a longitudinal axis 113 and having disposed therein a vibrating agitation mechanism 114. A control element 116 is adapted to control operation of vibrating agitation mechanism 114, and at least one power source 118 provides power to vibrating agitation mechanism 114 and control element 116.

A hollow medicament compartment housing 120 is associated with capsule housing 112. Medicament compartment housing 120 defines a hollow 122 dimensioned and configured to have medicament tablet 102 disposed therein. At least one aperture 124 is formed in medicament compartment housing 120, the aperture being dimensioned and configured to enable fluid communication between an environment surrounding medicament compartment housing 120 and hollow 122.

In some embodiments, apertures 124 are dimensioned and configured such that, when medicament tablet 102 is disposed within hollow 122 and device 100 is in the gastrointestinal tract of the user, the ingestible medicament of medicament tablet 102 enters the environment surrounding medicament compartment housing 120 for delivery thereof to the body of the user.

In some embodiments, medicament compartment housing 120 also includes at least one biasing mechanism 126 adapted, when medicament tablet 102 is disposed within hollow 122, to bias medicament tablet 102 toward capsule housing 112 of capsule 110. As described in further detail hereinbelow, the biasing mechanism 126 may include any type of spring or springy element, and/or any type of pre-loaded element, such as a compression spring, a spring-loaded leaf, a pre-loaded plunger, and the like.

Relating specifically to capsule 110, power source 118 may be any suitable power source, such as one or more alkaline or silver oxide batteries, primary batteries, rechargeable batteries, capacitors and/or supercapacitors.

Intermittently activated vibrating agitation mechanism 114 is adapted to have a vibration mode of operation (also termed the first mode of operation) and a rest mode of operation (also termed the second mode of operation). In the vibration mode of operation, intermittently activated vibrating agitation mechanism 114 is adapted to exert forces on capsule housing 112, such that capsule housing 112 exerts vibrations on an environment surrounding capsule 110 and/or device 100.

In some embodiments, the capsule 110 is in an inoperative state, until the receipt of an activation input, which causes control element 116 to transition the capsule from the inoperative state to an operative state.

In some embodiments, control element 116 is functionally associated with, or includes, a timing mechanism 130, powered by power source 118 and adapted to track at least one time characteristic, such as a duration that has passed since an activation input was received, or a duration that has passed since the user ingested capsule 110.

In some embodiments, capsule 110 is devoid of any sensors for sensing an environment thereof. In some such embodiments, control element 116 is adapted, in response to receipt of an activation input, to wait a predetermined delay time, and following the predetermined delay time, to activate vibrating agitation mechanism 114 to operate in said first vibration mode of operation.

In other embodiments, such as the embodiment illustrated in FIG. 1, capsule 110 further includes at least one sensor 132, functionally associated with control element 116. The at least one sensor 132 may be adapted to sense at least one parameter within capsule 110 or in an environment of capsule 110, and may include a temperature sensor, an illumination sensor, a moisture sensor, a pressure sensor, an accelerometer, or any other suitable sensor. In some embodiments, the at least one sensor 132 is adapted to identify a specific condition in capsule 110 or in the vicinity thereof, and to provide an activation input to control element 116 in response to identification of the condition. For example, in some embodiments the condition is indicative of the user ingesting capsule 110.

For example, in some embodiments sensor 132 may include an illumination sensor, adapted to identify transition of capsule 110 from an illuminated environment (e.g. outside the human body) to a dark environment (e.g. within the human body) and to provide an activation input in response to identification of such a transition.

As another example, in some embodiments sensor 132 may include a motion or acceleration sensor, such as an accelerometer, adapted to identify an activation motion carried out by a user on capsule 110 or on device 100 and to provide an activation input in response to identification of such a transition. An example of an accelerometer providing an activation input for a gastrointestinal capsule is provided in U.S. Pat. No. 10,314,514, which is incorporated by reference for all purposes as if fully set forth herein.

As another example, in some embodiments sensor 132 may include a pressure sensor adapted identify pressure applied to the capsule 110 or to device 100, which pressure is indicative of the capsule moving through a pharynx of the user, and to provide an activation input in response to identification of such pressure.

As a further example, in some embodiments sensor 132 may include a temperature sensor adapted to identify transition of capsule 110 or of device 100 from an area with ambient temperature (e.g. outside the human body) to an area with a human body temperature and to provide an activation input in response to identification of such a transition.

As a further example, in some embodiments sensor 132 may include a moisture sensor adapted to identify transition of capsule 110 or of device 100 from a dry area (e.g. outside the human body) to a moist area (e.g. within the human body) and to provide an activation input in response to identification of such a transition.

It will be appreciated by people of skill in the art that sensor 132 need not necessarily be disposed within capsule 110, as illustrated in FIG. 1, and may be disposed anywhere within device 100, for example within hollow 122 of medicament compartment housing 120, on an exterior of capsule 110, or on the exterior of device 100.

In some embodiments, device 100 may be functionally associated with a control unit 140, which may be remote from device 100 and from capsule 110, and which is adapted to provide one or more inputs to the capsule. In some such embodiments, capsule 110 further includes a remote input receiving mechanism 136, functionally associated with control element 116, and adapted to receive inputs from an input providing mechanism 142 of control unit 140.

In some embodiments, control unit 140 may further include a timing mechanism 146, adapted to track at least one time characteristic, such as a duration that has passed since a control instruction was provided to capsule 110.

In some embodiments, control unit 140 may further include a user input receiver 148, such as a keyboard, touch screen, or touch pad, adapted to receive input from a user, such as the user, a medical professional treating the user, or a caregiver of the user.

Control unit 140 may be any suitable type of control unit. In some embodiments, control unit may be a suitably configured smart phone or a tablet computer.

In some such embodiments, control unit 140 may provide inputs to capsule 110 by remotely transmitting the inputs from input providing mechanism 142 to remote input receiving mechanism 136, for example using a short range wireless communication method, such as radio frequency (RF) communication or Bluetooth® communication. One example of such a mechanism for providing input to a capsule is described in U.S. Pat. No. 10,478,373, which is incorporated by reference for all purposes as if fully set forth herein.

In some embodiments, control unit 140 is adapted to provide the activation input to control element 116 of capsule 110. In some such embodiments, control unit 140 provides the activation input prior to the user ingesting device 100 including capsule 110, whereas in other embodiments control unit 140 provides the activation input following ingestion of device 100 and capsule 110 by the user.

Relating to the characteristics of vibrating agitation mechanism 114, the vibrating agitation mechanism may be any suitable mechanism that can be intermittently activated and can apply suitable forces onto capsule housing 112.

In some embodiments, intermittently activated vibrating agitation mechanism 114 may include a radial agitation mechanism adapted to exert radial forces on capsule housing 112, in a radial direction with respect to the longitudinal axis of housing 112. For example, the radial agitation mechanism may include an unbalanced weight attached to a shaft of an electric motor powered by said battery, substantially as described in U.S. Pat. No. 9,707,150, which is incorporated by reference for all purposes as if fully set forth herein.

In some embodiments, intermittently activated vibrating agitation mechanism 114 may include an axial agitation mechanism adapted to exert radial forces on the capsule housing 112, in an axial direction with respect to a longitudinal axis of housing 112. For example, the axial agitation mechanism may include an electric motor powered by the battery and an urging mechanism, associated with, and driven by, the electric motor, such that the urging mechanism adapted to exert said axial forces, substantially as described in U.S. Pat. No. 9,707,150. In some embodiments, the urging mechanism adapted to exert the axial forces in opposite directions. In some embodiments, the urging mechanism is adapted to deliver at least a portion of the axial forces in a knocking mode.

In some embodiments, the forces exerted by intermittently activated vibrating agitation mechanism 114 on capsule housing 112 in the vibration mode of operation include radial forces in a radial direction with respect to the longitudinal axis of the housing and axial forces in an axial direction with respect to the longitudinal axis. In some embodiments, a single agitation mechanism exerts both the radial and the axial forces. In other embodiments, the axial forces are exerted by one agitation mechanism, and the radial forces are exerted by another, separate, agitation mechanism, where both agitation mechanisms form part of intermittently activated vibrating agitation mechanism 114.

In some embodiments, the intermittently activated vibrating agitation mechanism 114 may include a magnet mounted onto a rotor adapted to exert a magnetic field as well as radial forces on capsule housing 112. For example, such a magnetic vibration agitation mechanism is described in US Patent Application Publication No. 2016/0310357, which is incorporated by reference for all purposes as if fully set forth herein.

In some embodiments, housing 112 may include first and second members, and vibrating agitation mechanism 114 may include a mechanism adapted to effect a vibration by moving the first member of the housing in the opposite direction relative to the second member of the housing, substantially as described in U.S. Pat. No. 9,078,799, which is incorporated by reference for all purposes as if fully set forth herein.

In some embodiments, housing 112 may include a vibration agitation mechanism 114 which makes use of a pendulum to cause vibration in the vicinity of the capsule, for example as described in CN Patent Application Number 105997466 filed on Jun. 16, 2016, which is incorporated by reference for all purposes as if fully set forth herein.

In some embodiments, or at some times, control element 116 is adapted to control vibration agitation mechanism 114, and specifically to set at least one vibration parameter of vibration agitation mechanism 114, so as to promote absorption of the ingestible medicament into the bloodstream of the user. For example, absorption of the ingestible medicament may be promoted by the vibration breaking down the medicament tablet to smaller, more absorbable parts. As another example, absorption of the ingestible medicament may be promoted by the vibration promoting emulsification of the ingestible medicament. As yet another example, absorption of the ingestible medicament may be promoted by the vibration causing a hydrophobic phase of the ingestible medicament to form smaller bubbles, thereby increasing the surface area of the hydrophobic phase for absorption thereof. In another example, absorption of the ingestible medicament may be promoted by the vibration causing greater exposure of the ingestible medicament to the environment.

In some embodiments, or at some times, control element 116 may be adapted to control vibrating agitation mechanism 114 so that the capsule applies forces to an environment thereof, such that within the gastrointestinal tract, a mechanical stimulation of the wall of the gastrointestinal tract is effected.

In some such embodiments, the at least one vibration parameter includes at least one of a vibration frequency, a cumulative vibration duration, a number of vibration cycles per time unit, a duration of a vibration duration within a vibration cycle, a duration of a repose duration within a vibration cycle, a total duration of a single vibration cycle, and a net force exerted by said housing on said environment, as explained in further detail hereinbelow.

In some embodiments, control element 116 is adapted to control a timing or activation delay of the vibration mode of operation of the vibration agitation mechanism 114 such that the vibration mode of operation at least partially transpires within an estimated absorption time period of the ingestible medicament released from medicament tablet 102 within the gastrointestinal tract of the user.

In some embodiments, control element 116 is adapted to control a timing or activation delay of the vibration mode of operation of the vibration agitation mechanism 114 such that the vibration mode of operation at least partially transpires within an actual absorption time period of the ingestible medicament released from medicament tablet 102 within the gastrointestinal tract of the user.

In the vibrating mode of operation, intermittently activated vibrating agitation mechanism 114 is adapted to have a plurality of vibration cycles, where each cycle includes a vibration duration followed by a repose duration. Forces are exerted by the vibrating agitation mechanism 114 on capsule housing 112 only during the vibration duration, and as such, capsule housing 112 only exerts forces on an environment thereof during the vibration duration.

In some embodiments, the number of vibration cycles per hour is in the range of 20 to 400, 40 to 400, 60 to 400, 80 to 400, 40 to 380, 60 to 380, 80 to 380, 40 to 360, 60 to 360, 80 to 360, 100 to 360, 100 to 330, 100 to 300, 100 to 280, 100 to 250, 100 to 220, 100 to 200, 120 to 300, 120 to 280, 120 to 250, 120 to 220, 120 to 200, 150 to 300, 150 to 280, 150 to 250, 150 to 220, 150 to 200, 170 to 300, 170 to 250, 170 to 220, or 170 to 200.

In some embodiments, the repose duration is greater than the vibration duration.

In some embodiments, the vibration duration is in the range of 0.1 second to 10 seconds, 1 second to 10 seconds, 1 second to 9 seconds, 2 seconds to 9 seconds, 3 seconds to 9 seconds, 3 seconds to 8 seconds, 3 seconds to 7 seconds, 3 seconds to 6 seconds, 4 seconds to 6 seconds, or 5 seconds to 6 seconds.

In some embodiments, the repose duration is in the range of 1 second to 180 seconds, 3 seconds to 180 seconds, 5 seconds to 180 seconds, 5 seconds to 150 seconds, 5 seconds to 120 seconds, 8 seconds to 100 seconds, 8 seconds to 30 seconds, 10 seconds to 80 seconds, 10 seconds to 70 seconds, 10 seconds to 60 seconds, 10 seconds to 50 seconds, 10 seconds to 40 seconds, 10 seconds to 30 seconds, 10 seconds to 20 seconds, or 15 seconds to 20 seconds.

In some embodiments, the total duration of one vibration cycle is in the range of 1.1 seconds to 200 seconds, 5 seconds to 200 seconds, 10 seconds to 200 seconds, 10 seconds to 150 seconds, 10 seconds to 100 seconds, 10 seconds to 80 seconds, 10 seconds to 50 seconds, 10 seconds to 40 seconds, 10 seconds to 30 seconds, 15 seconds to 50 seconds, 15 seconds to 40 seconds, 15 seconds to 30 seconds, or 15 seconds to 25 seconds.

In some embodiments, the cumulative duration of the vibrating mode of operation, or the cumulative duration during which vibration cycles are occurring, is in the range of 1 hour to 12 hours, 2 hours to 10 hours, 2 hours to 8 hours, 2 hours to 6 hours, 2 hours to 4 hours, or 2 hours to 3 hours.

It will be appreciated that the cumulative duration of vibration cycles may be dependent on properties of power source 118.

It will be appreciated by persons skilled in the art that the vibration mode of operation may be intermittent, or interrupted, such that vibrating agitation mechanism 114 is operative in the vibration mode for a first duration, for example 30 minutes, then does have any vibration cycles for a second duration, for example 1 hour, and then is operative in the vibration mode and has vibration cycles for a third duration, for example two hours. The cumulative duration relates to the sum of all durations during which vibrating agitation mechanism 114 was operative in the vibration mode and included vibration cycles, including the vibration duration and the repose duration of the vibration cycle.

In some embodiments, vibrating agitation mechanism 114 is configured to exert forces on the capsule housing 112, such that a net force exerted by the capsule housing 112 on the environment thereof is in the range of 50 grams force (gf) to 600 gf, 50 gf to 550 gf, 100 gf to 550 gf, 100 gf to 500 gf, 150 gf to 500 gf, 200 gf to 500 gf, or 200 gf to 450 gf.

In some embodiments, vibrating agitation mechanism 114 is configured to exert said forces on capsule housing 112 to attain a capsule housing 112 vibrational frequency within a range of 10 Hz to 650 Hz, 15 Hz to 600 Hz, 20 Hz to 550 Hz, 30 Hz to 550 Hz, 50 Hz to 500 Hz, 70 Hz to 500 Hz, 100 Hz to 500 Hz, 130 Hz to 500 Hz, or 150 Hz to 500 Hz.

It will be appreciated that the exact specifications of the capsule, such as the specific frequency and force ranges applicable to a specific capsule, are dependent on the specifications of the power source 118 and of the vibrating agitation mechanism 114.

It will be further appreciated that a specific capsule may be controlled by the control element 116 such that different vibrational frequencies may be attained and/or different net forces may be exerted, by the capsule in different vibration cycles of the capsule. Due to the natural distinction between users, use of multiple different parameters in different vibration cycles of a single capsule would allow the capsule to successfully treat multiple users, even if the personal optimal treatment for those users is not the same, as there is a higher chance that in at least some of the vibration cycles the activation parameters of the capsule would reach, or be close to, the optimal parameters for each specific user.

Control element 116 is adapted to control the operation of intermittently activated vibrating agitation mechanism 114. Such control may include control of any one or more of the force applied by the vibrating agitation mechanism 114, the vibrational frequency reached, the times in which vibrating agitation mechanism 114 operates in the vibration mode of operation, the vibration duration of each vibration cycle, the repose duration of each vibration cycle, the vibration cycle duration, and cumulative vibration duration of the vibrating agitation mechanisms.

In some embodiments, control element 116 is adapted to receive information relating to the desired vibration protocol from control unit 140, prior to ingestion of device 100 and capsule 110 or to activation of the capsule, or during the device's and capsule's traversal of the user's GI tract. For example, the information may be remotely transmitted from control unit 140 to control element 116, for example using a short range wireless communication method. In some embodiments, the information is transmitted as a list of vibration parameters for effecting the vibration protocol. In some embodiments, the information is transmitted as executable code for effecting the first vibration protocol.

In some embodiments, the information includes a desired number of vibration cycles, a desired vibration duration in each vibration cycle, a desired repose duration in each vibration cycle, a desired cumulative vibration duration, and the like.

Relating to hollow medicament compartment housing 120, in some embodiments, medicament compartment housing 120 is biodegradable. In some embodiments, medicament compartment housing 120 is digestible by the gastrointestinal tract of the user. In some embodiments, medicament compartment housing 120 is flexible.

In some embodiments, hollow 122 has a volume in the range of 200 mm$^3$ to 800 mm$^3$, 300 mm$^3$ to 700 mm$^3$, 400 mm$^3$ to 600 mm$^3$, or 500 mm$^3$.

In some embodiments, apertures 124 are dimensioned and configured such that medicament tablet 102, while whole, cannot be removed from hollow 122 of medicament compartment housing 120.

In other embodiments, apertures 124 are dimensioned and configured to enable insertion of medicament tablet 102, via at least one aperture, into hollow 122 of medicament compartment housing 120.

Ins some embodiments, in use during transition of the device 100 through the gastrointestinal tract of the user, biasing mechanism 126 is adapted to continue biasing medicament tablet 102 toward housing 112 of vibrating ingestible capsule 110, while the ingestible medicament from medicament tablet 102 is delivered to the environment surrounding hollow 122 and device 100.

In some embodiments, biasing mechanism 126 includes at least one pre-loaded compression spring, for example as illustrated in FIGS. 5A and 5B, described in detail hereinbelow. In some embodiments, biasing mechanism 126 includes at least one flexible and resilient leaf, for example as illustrated in FIGS. 6A and 6B, described in detail hereinbelow.

In some embodiments, biasing mechanism 126 includes at least one longitudinal biasing mechanism adapted to bias medicament tablet 102 by application of pressure along a longitudinal axis of the medicament tablet, for example as illustrated in FIGS. 5A and 5B described in detail hereinbelow.

Figure 6A:
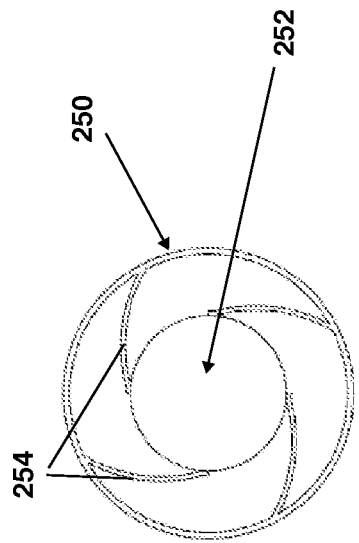
FIGS. 6A and 6B are, respectively, partial sectional illustrations of a device similar to the device of FIG. 2 and having a radial medicament tablet biasing mechanism, at two times during use thereof, according to another embodiment of the present invention.
Figure 6B:
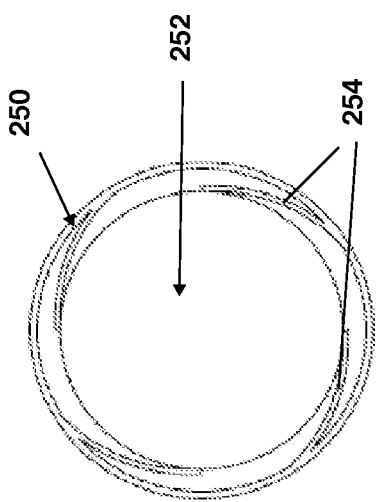

In some embodiments, biasing mechanism 126 includes at least one radial biasing mechanism adapted to bias medicament tablet 102 by application of radial pressure along a perimeter of the medicament tablet, for example as illustrated in FIGS. 6A and 6B described in detail hereinbelow.

In some embodiments, an exterior contour of at least a portion of housing 112 of the vibrating ingestible capsule 110 is adapted to match an exterior contour of the medicament tablet 102, for example as illustrated in FIGS. 3B and 4B described in detail hereinbelow. In some such embodiments, the exterior contour of at least a portion of housing 112 is concave as illustrated in FIG. 3B.

In some embodiments, medicament compartment housing 120 is at least partially attached to housing 112 of vibrating ingestible capsule 110. In some embodiments, medicament compartment housing 120 is fully attached to housing 112 of vibrating ingestible capsule 110.

In some embodiments, medicament compartment housing 120 is fixedly attached to housing 112 of vibrating ingestible capsule 110, for example by adhering, by soldering, or by snap fit engagement. In other embodiments, medicament compartment housing 120 is removably attached to housing 112 of vibrating ingestible capsule 110, for example by threaded engagement.

In some embodiments, housing 112 of vibrating ingestible capsule 110 includes an attachment mechanism, and medicament compartment housing 120 includes a corresponding attachment mechanism, for mutual attachment of vibrating ingestible capsule 110 to hollow medicament compartment housing 120. An exemplary arrangement of such attachment mechanisms is illustrated, for example, in FIGS. 3B and 4B described in detail hereinbelow.

In some embodiments, medicament compartment housing 120 at least partially envelops housing 112 of vibrating ingestible capsule 110, as illustrated, for example, in FIGS. 7A to 8B.

In some embodiments, medicament compartment housing 120 fully envelops housing 112 of vibrating ingestible capsule 110. In some such embodiments, medicament compartment housing 120 includes a hollow capsule including aperture(s) 124, which has greater length than the length of vibrating ingestible capsule 110, and a greater diameter than a diameter of vibrating ingestible capsule. In such embodiments, vibrating ingestible capsule 110 is disposed within the hollow capsule of the medicament compartment housing.

Turning now to characteristics of the medicament tablet 102, in some embodiments, medicament tablet 102 has a diameter of up to 5 mm, up to 6 mm, up to 7 mm, up to 8 mm, or up to 9 mm.

In some embodiments, medicament tablet 102 has a maximal linear dimension, in any direction of the tablet, of up to 10 mm.

In some embodiments, medicament tablet 102 has a height of up to 3 mm, up to 4 mm, or up to 5 mm.

In some embodiments, medicament tablet 102 has a volume of up to 100 mm$^3$, up to 150 mm$^3$, up to 200 mm$^3$, up to 250 mm$^3$, or up to 300 mm$^3$.

In some embodiments, the ingestible medicament of medicament tablet 102 is absorbable or at least partially absorbable in the stomach of the user. In some embodiments, the ingestible medicament of medicament tablet 102 is absorbable or at least partially absorbable in the small intestine of the user.

In some embodiments, the ingestible medicament of medicament tablet 102 is suitable for treatment of one or more symptom or disease, selected from the group consisting of: Parkinsonism; Parkinson's Disease; progressive supranuclear palsy; corticobasal degeneration; multiple system atrophy; Parkinson-plus syndromes (also known as disorders of multiple system degeneration); any neurodegenerative disease in which the subject exhibits at least one (and typically at least two or three) of the classical features of Parkinson's disease: tremor, postural instability, and akinesia or bradykesia; any neurodegenerative disease in which the subject positively responds to a dopaminergic treatment; any neurodegenerative disease in which the particular subject positively responds to an anticholinergic treatment; Constipation; Crohn's disease; Gastroparesis; irritable bowel syndrome (IBS); diarrhea or loose bowel movements; colitis; Hirschsprung's disease; Dyspepsia; and dysphagia.

In some embodiments, the ingestible medicament of medicament tablet 102 comprises or includes an ingestible medicament selected from the group consisting of: levodopa; at least one dopaminergic agent; at least one catecholamine precursor; a dopamine precursor; at least one dopamine precursor agent; (L)-3,4-dihydroxyphenylalanine; N-methyl-N-(2-propynyl)-2-methyl-1-phenylethyl-2-amine; tyrosine hydroxylase; apomorphine; at least one anticholinergic agent; at least one agent selected to antagonize at least one cholinergic receptor; benzhexol; orphenadrine; at least one selective allosteric potentiator of metabotropic glutamate receptor 4 (mGluR4); N-phenyl-7-(hydroxylimino)cyclopropa[b]chromen-1a-carboxamide; at least one osmotic agent; magnesium citrate; magnesium hydroxide; polyethylene glycol; sodium phosphate; MiraLAX®; at least one contraction stimulating agent; bisacodyl; senna; Correctol; Ducodyl; Dulcolax; Senexon; Senokot; at least one stool softening agent; docusate sodium; Colace; Linaclotide; Lactulose; lubiprostone; plecanatide; prucaltride; loperamide; and bismuth subsalicylate.

Figure 3A:
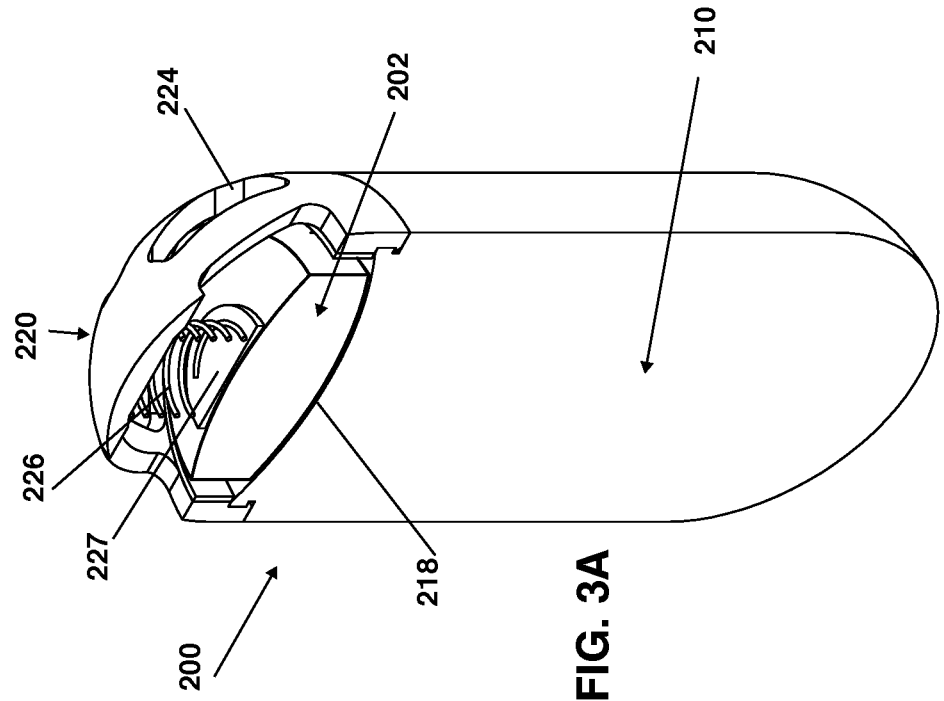
Figure 4A:
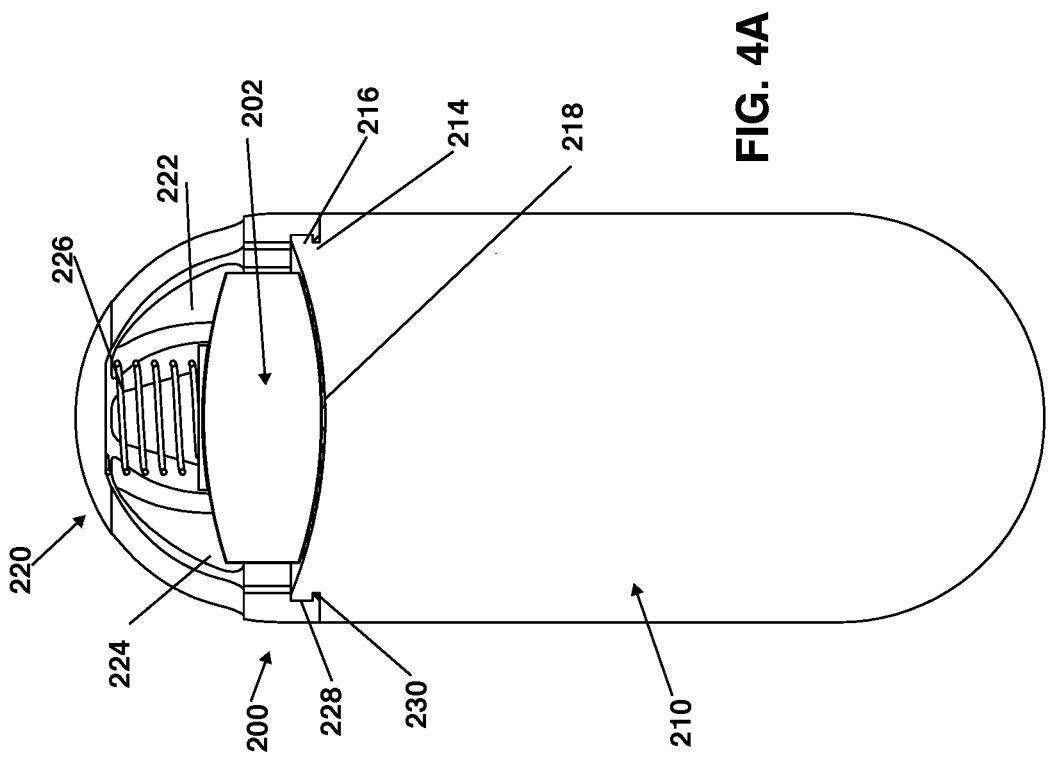

Reference is now made to FIGS. 2A and 2B are, respectively, a perspective view illustration and a planar side view illustration of a first embodiment of a device 200 for delivering an ingestible medicament into the gastrointestinal tract of a user, the device having a medicament tablet 202 including the ingestible medicament disposed therein, according to an embodiment of the present invention, to FIGS. 3A and 3B which are, respectively, a complete and a partial perspective sectional illustration of device 200 and medicament tablet 202 disposed therein, and to FIGS. 4A and 4B which are, respectively, a complete and a partial planar sectional illustration of device 200 having medicament tablet 202.

As seen, device 200, which is arranged along a longitudinal axis 204, includes a vibrating ingestible capsule 210 including a housing 212, substantially as described hereinabove with respect to FIG. 1. It will be appreciated that capsule 210 includes at least a vibrating agitation mechanism, a control element, and a power source, as described hereinabove with respect to FIG. 1, even though these components are not explicitly shown in FIGS. 2A to 4B.

A hollow medicament compartment housing 220, here illustrated as having the shape of a convex dome, defines a hollow 222 in which is disposed medicament tablet 202. A plurality of apertures 224 are formed about the perimeter of medicament compartment housing 220. In the illustrated embodiment, the apertures 224 are not large enough to allow passage of the whole medicament tablet 202 therethrough, although in other embodiments the apertures may be sized and configured to allow a user to insert the medicament tablet into hollow 222 via one of the apertures 224.

Hollow medicament compartment housing 220 is attached to vibrating ingestible capsule 210. In the illustrated embodiment, housing 212 of vibrating ingestible capsule 210 includes a first attachment mechanism in the form of a circumferential slot 214 and a circumferential protrusion 216 disposed adjacent a longitudinal end 218 of capsule housing 212. Hollow medicament compartment housing includes a second, corresponding attachment mechanism in the form of a circumferential slot 228 and a circumferential protrusion 230 disposed adjacent an end 232 of medicament compartment housing 220. Circumferential slot 228 corresponds in dimensions to circumferential protrusion 216 of capsule 210, and circumferential protrusion 230 corresponds in dimensions to circumferential slot 214 of capsule 210.

In the illustrated embodiment, medicament compartment housing 220 is fixedly attached to vibrating ingestible capsule 210 by snap fit engagement of slot 228 with protrusion 216 and snap fit engagement of protrusion 230 with slot 214. However, any type of attachment between medicament compartment housing 220 and vibrating ingestible capsule 210 is considered within the scope of the present invention, including threaded engagement, engagement by soldering, engagement by adhesive, and the like.

As seen clearly in FIGS. 3A to 4B, an exterior surface of longitudinal end 218 of capsule housing 212 is concave, and has an exterior contour which matches an exterior contour of medicament tablet 202. However, it will be appreciated that this structure is not necessary, and that medicament tablet 202 may engage any portion of the capsule housing 212, along a surface of the capsule housing, along a surface of the medicament tablet, or tangentially.

A biasing mechanism in the form of a compression spring 226, terminating in a compression plate 227, extends from the interior surface of hollow medicament compartment housing 220 toward medicament tablet 202. Compression spring 226 and compression plate 227 bias medicament tablet 202 toward an exterior surface of housing 212 of vibrating ingestible capsule 210. In the illustrated embodiment, the compression spring and compression plate extend from an apex of the dome of medicament compartment housing 220, and apply pressure to medicament tablet 202 in a longitudinal direction, along a longitudinal axis of the medicament tablet and of device 200. However, any other suitable arrangement of the biasing mechanism is considered to be within the scope of the invention, as described hereinbelow with respect to FIGS. 6A and 6B.

Reference is now additionally made to FIGS. 5A and 5B, which are, respectively, partial sectional illustrations of device 200, at two times during use thereof. As seen, in FIG. 5A, the medicament tablet 202 is larger, or is whole, and is compressed by compression spring 226 and compression plate 227 against end 218 of housing 212 of the vibrating ingestible capsule 210. At a later time, occurring for example after the device 200 has been ingested and the medicament tablet 202 has been exposed to gastric fluids, the medicament tablet is significantly smaller than it was at the starting time. However, the compression spring 226 and compression plate 227 continue to bias the medicament tablet against the end 218 of capsule housing 212.

As such, it is appreciated that the longitudinal biasing mechanism illustrated in FIGS. 5A and 5B of the present invention "follows" the medicament tablet, and continues to bias the medicament tablet in a desired direction during changes to the dimensions of the medicament tablet, and during absorption of the medicament therefrom.

Reference is now additionally made to FIGS. 6A and 6B, which are, respectively, partial sectional illustrations of a device similar to device 200 and having a radial biasing mechanism, at two times during use thereof, according to another embodiment of the present invention. Specifically, sectional illustrations 6A and 6B are taken in a direction perpendicular to the longitudinal axis of the device, through the center of the medicament tablet.

As seen in FIGS. 6A and 6B, a hollow medicament compartment housing 250 has a medicament tablet 252 disposed therein. A biasing mechanism, including a plurality of flexible and resilient leaves 254 extending radially inwardly from an interior surface of hollow medicament compartment housing 250 applies pressure, in a radial direction, to a perimeter of medicament tablet 252, so as to bias the medicament tablet toward the center of medicament compartment housing 250 and to hold it in place there.

As seen, in FIG. 6A, the medicament tablet 252 is larger, or is whole, and is held by biasing leaves 254 to be concentric with a hollow medicament compartment housing 250. At a later time, occurring for example after the device has been ingested and the medicament tablet 252 has been exposed to gastric fluids, the medicament tablet is significantly smaller than it was at the starting time. However, the biasing leaves 254 continue to bias the medicament tablet 252 to be concentric with a hollow medicament compartment housing 250.

As such, it is appreciated that the radial biasing mechanism illustrated in FIGS. 6A and 6B of the present invention "follows" the medicament tablet, and continues to bias the medicament tablet in a desired direction during changes to the dimensions of the medicament tablet, and during absorption of the ingestible medicament therefrom.

Figure 7A:
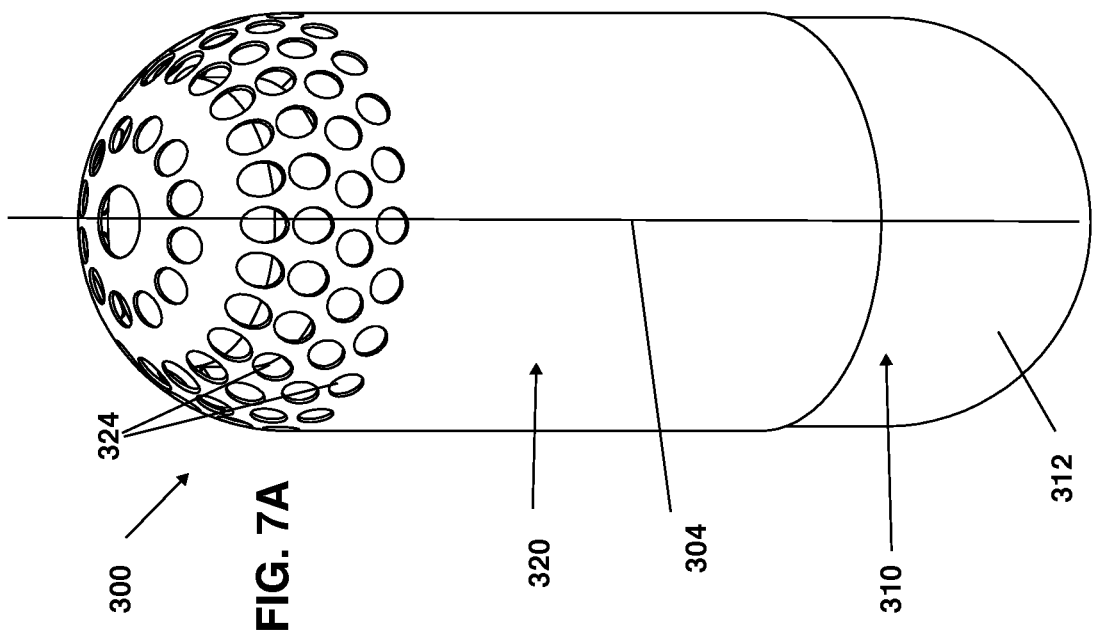
FIGS. 7A and 7B are, respectively, a perspective view illustration and a planar view illustration of a second embodiment of a device for delivering an ingestible medicament into the gastrointestinal tract of a user, the device having a medicament tablet including the ingestible medicament disposed therein, according to yet another embodiment of the present invention.
Figure 7B:
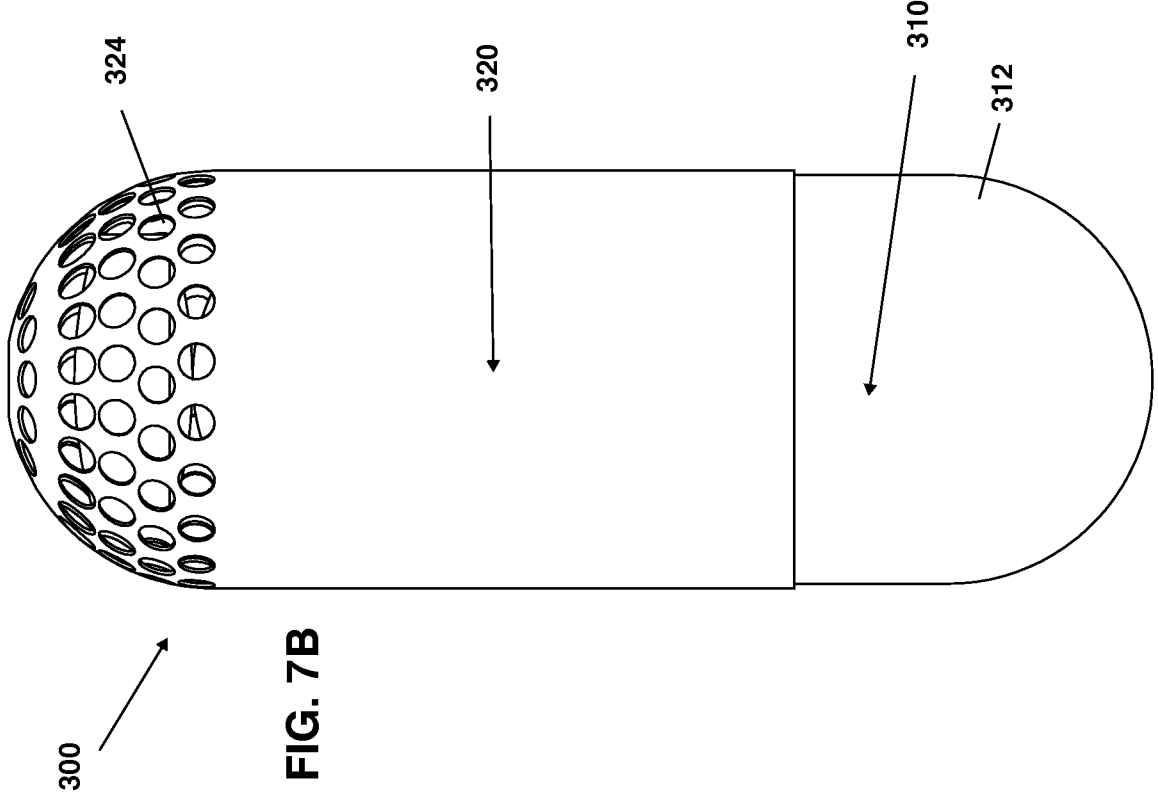
Figure 8B:
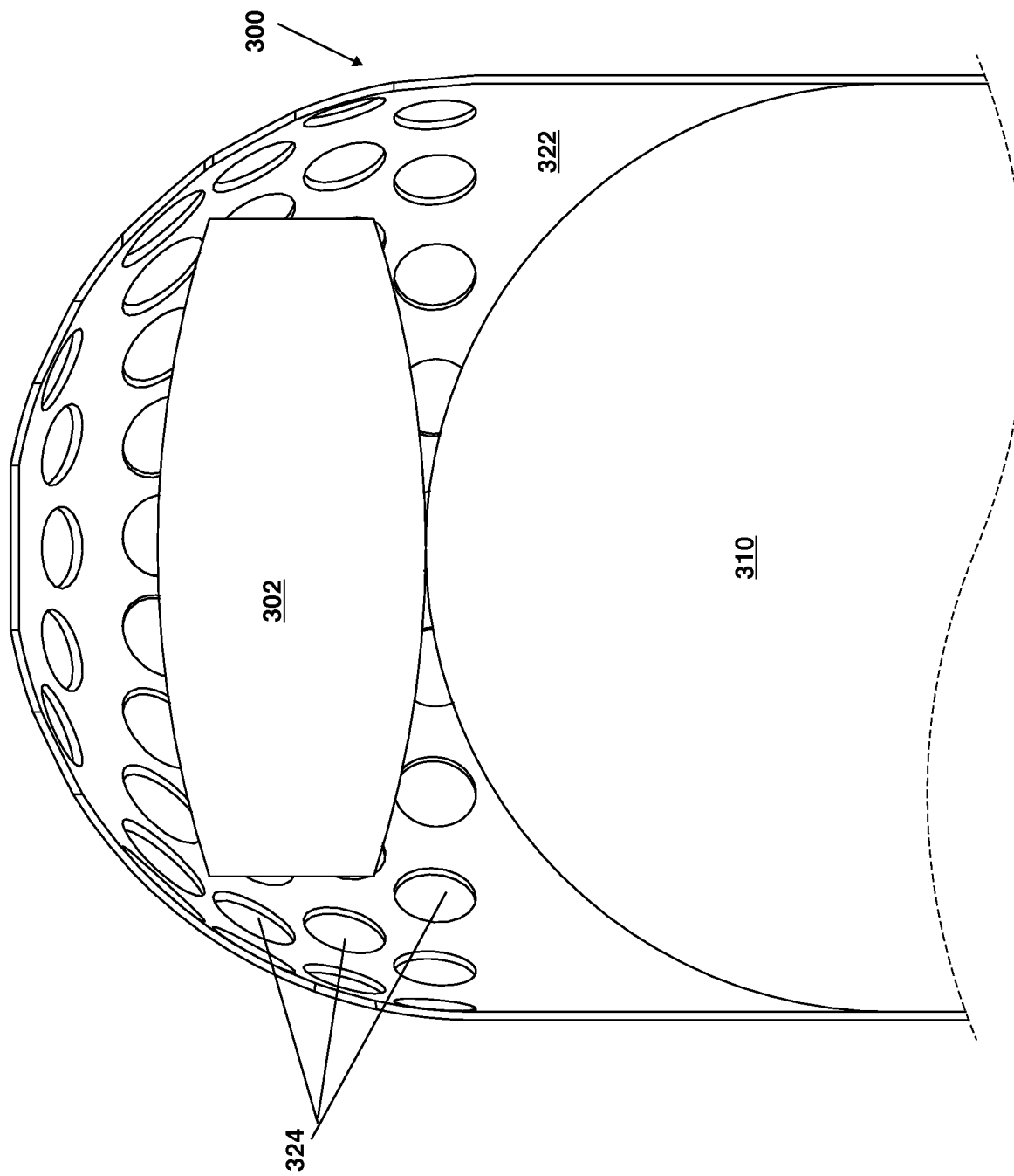

Reference is now made to FIGS. 7A and 7B, which are, respectively, a perspective view illustration and a planar view illustration of a second embodiment of a device 300 for delivering an ingestible medicament into the gastrointestinal tract of a user, the device having a medicament tablet 302 including the ingestible medicament disposed therein, according to yet another embodiment of the present invention, and to FIGS. 8A and 8B, which are, respectively, a complete and a partial planar sectional illustration of device 300 having medicament tablet 302 disposed therein.

As seen, device 300, which is arranged along a longitudinal axis 304, includes a vibrating ingestible capsule 310 including a housing 312, substantially as described hereinabove with respect to FIG. 1. It will be appreciated that capsule 310 includes at least a vibrating agitation mechanism, a control element, and a power source, as described hereinabove with respect to FIG. 1, even though these components are not explicitly shown in FIGS. 7A to 8B.

A hollow medicament compartment housing 320, here illustrated as having the shape of a convex domed sleeve, defines a hollow 322 in which is disposed medicament tablet 302. A plurality of circular apertures 324 are formed about the perimeter of medicament compartment housing 320. In the illustrated embodiment, the apertures 324 are not large enough to allow passage of the whole medicament tablet 302 therethrough, although in other embodiments the apertures may be sized and configured to allow a user to insert the medicament tablet into hollow 322 via one of the apertures 324.

Hollow medicament compartment housing 320 partially envelops vibrating ingestible capsule 310. In some embodiments, the medicament compartment housing may frictionally engage housing 312 of capsule 310.

In other embodiments, not illustrated, hollow medicament compartment housing 320 may fully envelop ingestible vibrating capsule 310. In some such embodiments, hollow medicament compartment housing 320 may form a hollow capsule, having a greater diameter than capsule 310 and a greater length than capsule 310, such that capsule 310 as well as medicament tablet 302 may be disposed, adjacent one another, within the capsule of medicament compartment housing 320.

As seen in FIGS. 8A and 8B, medicament tablet 302 is disposed within and engages housing 31A2 of vibrating ingestible capsule 310, without being actively biased toward the capsule 310. As such, when capsule 310 is in its operative vibration mode, vibration of the capsule 310 affects the tablet 302 as well as the medicament compartment housing 320 surrounding the capsule 310, and promotes absorption of the ingestible medicament from tablet 302 substantially as described hereinabove.

Reference is now additionally made to FIG. 9, which is a schematic flowchart of a method for delivering an ingestible medicament of a medicament tablet into the gastrointestinal tract of user according to the present invention. The method may be based on the use of a device including a vibrating ingestible capsule and a medicament tablet, as described hereinabove with reference to FIGS. 1 to 8B.

As seen at step 400, a device, such as device 100, 200, or 300 described hereinabove, including a vibrating ingestible capsule and a hollow medicament compartment housing, is provided to a user.

At step 402, the vibrating ingestible capsule and the hollow medicament compartment housing are associated with one another. In some embodiments, step 402 may take place in a factory, prior to providing the device to the user at step 400. In other embodiments, the device may be provided to the user as two separate pieces, namely the ingestible vibrating capsule and the hollow medicament compartment housing, and the user carries out step 402 following receipt of the device at step 400.

In some embodiments, the associating at step 402 includes at least partially attaching the medicament compartment housing to the vibrating ingestible capsule.

In some embodiments, the associating at step 402 includes fully attaching the medicament compartment housing to the vibrating ingestible capsule.

In some embodiments, the associating at step 402 includes fixedly attaching the medicament compartment housing to the vibrating ingestible capsule.

In some embodiments, the associating at step 402 includes removably attaching the medicament compartment housing to the vibrating ingestible capsule.

In some embodiments, the associating at step 402 includes attaching the medicament compartment housing to the vibrating ingestible capsule by one or more of snap fit engagement, threaded engagement, adhering, soldering, or any other suitable mechanism of attachment.

In some embodiments, the associating at step 402 includes mutually attaching a first attachment mechanism on the vibrating ingestible capsule with a corresponding attachment mechanism on the medicament compartment housing, for example as described with respect to claims 2A to 5B.

In some embodiments, the associating at step 402 includes at least partially enveloping the medicament compartment housing around the vibrating ingestible capsule.

In some embodiments, the associating at step 402 includes fully enveloping the medicament compartment housing around the vibrating ingestible capsule.

In some embodiments, the device is provided to the user having the medicament tablet disposed within the hollow medicament compartment housing.

At step 404, the medicament tablet is inserted into the hollow medicament compartment housing. In some embodiments, step 404 may take place prior to associating the ingestible vibrating capsule with the hollow medicament compartment housing, either in a factory or by the user. In other embodiments, step 404 may be carried out following association of the ingestible vibrating capsule with the hollow medicament compartment housing, for example by insertion of the medicament tablet into the hollow via one of the apertures in the hollow medicament compartment housing. The medicament tablet inserted at step 404 may be any suitable type of medicament tablet, as described in detail hereinabove.

At step 406, the device, including the vibrating ingestible capsule, the hollow medicament compartment housing, and the medicament tablet, is ingested by the user, and begins to travel through the gastrointestinal tract of the user.

At step 408, which occurs following the user ingesting the device at step 406, the vibrating ingestible capsule is controlled such that the vibration mode of operation (e.g., when the vibration mode is initiated, a duration of the vibration mode, etc.) at least partially transpire within an absorption time period of the ingestible medicament included in the medicament tablet within the gastrointestinal tract of the user.

The absorption time period may be an estimated absorption time period, as defined herein, and/or an actual absorption time period as defined herein.

In some embodiment, step 408 may include controlling a timing of the vibration mode of operation such that the vibration mode at least partially transpires when the capsule is in a region of the gastrointestinal tract in which the ingestible medicament is typically absorbed into the bloodstream. The region of the gastrointestinal tract may include one or more of the stomach of the user, the duodenum of the user, the small intestine of the user, the large intestine of the user, or the colon of the user.

For example, when the medicament tablet includes the ingestible medicament levadopa, which is typically absorbed into the bloodstream through the stomach walls and/or the small intestine walls, the vibration mode at least partially transpires within a time period in which the device traverses, or is expected to traverse, the stomach and small intestine.

In some embodiments, step 408 includes setting at least one vibration parameter of the vibrating ingestible capsule of the device so as to promote absorption of the ingestible medicament into the bloodstream of the user. In some such embodiments, the at least one vibration parameter set at step 408 includes at least one of a vibration frequency, a cumulative vibration duration, a number of vibration cycles per time unit, a duration of a vibration duration within a vibration cycle, a duration of a repose duration within a vibration cycle, a total duration of a single vibration cycle, and a net force exerted by said housing on said environment.

In some embodiments, the controlling at step 408 includes controlling the vibration agitation mechanism such that the vibrating mode of operation includes a plurality of cycles, each of the cycles including a vibration duration followed by a repose duration, wherein the housing exerts the vibrations during the vibration duration.

In some embodiments, the repose duration is greater than the vibration duration.

In some embodiments, the vibration duration is in the range of 0.1 second to 10 seconds, 1 second to 10 seconds, 1 second to 9 seconds, 2 seconds to 9 seconds, 3 seconds to 9 seconds, 3 seconds to 8 seconds, 3 seconds to 7 seconds, 3 seconds to 6 seconds, 4 seconds to 6 seconds, or 5 seconds to 6 seconds.

In some embodiments, the repose duration is in the range of 1 second to 180 seconds, 3 seconds to 180 seconds, 5 seconds to 180 seconds, 5 seconds to 150 seconds, 5 seconds to 120 seconds, 8 seconds to 100 seconds, 8 seconds to 30 seconds, 10 seconds to 80 seconds, 10 seconds to 70 seconds, 10 seconds to 60 seconds, 10 seconds to 50 seconds, 10 seconds to 40 seconds, 10 seconds to 30 seconds, 10 seconds to 20 seconds, or 15 seconds to 20 seconds.

In some embodiments, a duration of each of the plurality of cycles is in the range of 1.1 seconds to 200 seconds, 5 seconds to 200 seconds, 10 seconds to 200 seconds, 10 seconds to 150 seconds, 10 seconds to 100 seconds, 10 seconds to 80 seconds, 10 seconds to 50 seconds, 10 seconds to 40 seconds, 10 seconds to 30 seconds, 15 seconds to 50 seconds, 15 seconds to 40 seconds, 15 seconds to 30 seconds, or 15 seconds to 25 seconds.

In some embodiments, the controlling at step 408 includes controlling the vibrating agitation mechanism such that a cumulative duration of the vibrating mode of operation is in the range of 1 hour to 12 hours, 2 hours to 10 hours, 2 hours to 8 hours, 2 hours to 6 hours, 2 hours to 4 hours, or 2 hours to 3 hours.

In some embodiments, the controlling at step 408 includes controlling the vibrating agitation mechanism to exert forces on the housing of the vibrating ingestible capsule, such that a net force exerted by the housing on the environment thereof is in the range of 50 grams force (gf) to 600 gf, 50 gf to 550 gf, 100 gf to 550 gf, 100 gf to 500 gf, 150 gf to 500 gf, 200 gf to 500 gf, or 200 gf to 450 gf.

In some embodiments, the controlling at step 408 includes controlling the vibrating agitation mechanism to exert the forces on the housing to attain a housing vibrational frequency within a range of 10 Hz to 650 Hz, 15 Hz to 600 Hz, 20 Hz to 550 Hz, 30 Hz to 550 Hz, 50 Hz to 500 Hz, 70 Hz to 500 Hz, 100 Hz to 500 Hz, 130 Hz to 500 Hz, or 150 Hz to 500 Hz.

In some embodiments, the method may also include step 410, in which the medicament tablet is biased toward the vibrating ingestible capsule. Step 410 may a continuous step, which begins when the medicament tablet is inserted into the hollow medicament compartment housing at step 404, and continues as long as the medicament tablet has not been removed from the hollow medicament compartment housing and has not been fully dissolved. More specifically, step 410 may continuously occur during ingestion of the device by the user at step 406, and in some embodiments during at least part of the duration controlling of the vibration agitation mechanism at step 408.

In some embodiments, the biasing at step 410 includes biasing the medicament tablet by application of pressure along a longitudinal axis of the medicament tablet.

In some embodiments, the biasing at step 410 includes biasing the medicament tablet by application of radial pressure along a perimeter of the medicament tablet.

In some embodiments, and as described in further detail herein, the method may include a further step 412 of transitioning the capsule (from an inoperative state) to an operative state.

The capsule may be pre-programmed with a vibration protocol. This protocol may include, by way of example, a particular or pre-determined activation time following ingestion, in which the capsule is transitioned from an inoperative state to an operative state. In such embodiments, the step 412 may be omitted from the method.

Alternatively or additionally, the capsule may receive an activation input in an active fashion (e.g., from an external controller via RF) or in a passive fashion (e.g., a signal from a sensor to the on-board controller), as described in detail hereinabove. It will be appreciated that step 412, in which the vibrating ingestible capsule is transitioned from the inoperative state to the operative state, may be performed prior to ingestion of the device by the user in step 406, or following such ingestion, for example in the case of external control via RF.

Substantially as described hereinabove, step 412 may be carried out, and the vibrating ingestible capsule may be activated, prior to the user ingesting the capsule at step 406, for example by a signal from the control unit or by the user carrying out an activation motion. In other embodiments, the activation input, and the transitioning of the capsule from being inoperative to being operative, occurs at the time of ingestion or immediately thereafter, for example by sensors sensing a change in the environment of the capsule due to its ingestion, as described at length hereinabove. In yet other embodiments, the transitioning of the capsule at step 412 may include the capsule receiving an activation input which is provided remotely when the capsule is already in the body of the user, for example by remote communication from control module 140.

In some embodiments, a control element of the vibrating ingestible capsule may optionally receive a desired vibration protocol for the user, at an optional step 414. In some embodiments, the programming of the desired vibration protocol at step 414 occurs at the time of manufacturing of the vibrating ingestible capsule or of the device, for example by pre-programming the protocol into the control element. In other embodiments, providing the desired vibration protocol for the user at step 414 may be effected by a control unit, such as control unit 140 of FIG. 1, as described in detail hereinabove with respect to FIG. 1.

Embodiments of the present invention are provided hereinbelow:

Embodiment 1. A device for delivering an ingestible medicament of a medicament tablet into the gastrointestinal tract of a user, the device including:
　a vibrating ingestible capsule including:
　　a housing;
　　a vibrating agitation mechanism disposed within the housing and adapted such that, in a vibration mode of operation, the housing exerts vibrations on an environment surrounding the vibrating gastrointestinal capsule;
　　a power supply disposed within the housing and adapted to power the vibrating agitation mechanism; and
　　a control element adapted to activate the vibrating agitation mechanism to be operative in the vibration mode of operation; and
　a hollow medicament compartment housing, associated with the housing, and having at least one aperture formed in the medicament compartment housing,
　wherein a hollow of the medicament compartment housing is dimensioned and configured to have the medicament tablet disposed therein, and
　wherein the at least one aperture is dimensioned and configured to enable fluid communication between an environment surrounding the medicament compartment housing and the hollow.

Embodiment 2. The device of embodiment 1, wherein the at least one aperture is dimensioned and configured such that, when the medicament tablet is disposed within the hollow and the device is in the gastrointestinal tract of the user, the ingestible medicament of the medicament tablet enters the environment surrounding the medicament compartment housing for delivery thereof to the body of the user.

Embodiment 3. The device of any one of embodiments 1 to 2, wherein at least one vibration parameter of the vibrating ingestible capsule is set so as to promote absorption of the ingestible medicament into the bloodstream of the user.

Embodiment 4. The device of embodiment 3, wherein the at least one vibration parameter includes at least one of a vibration frequency, a cumulative vibration duration, a number of vibration cycles per time unit, a duration of a vibration duration within a vibration cycle, a duration of a repose duration within a vibration cycle, a total duration of a single vibration cycle, and a net force exerted by the housing on the environment.

Embodiment 5. The device of any one of embodiments 1 to 4, further including at least one biasing mechanism adapted, when the medicament tablet is disposed within the hollow of the medicament compartment housing, to bias the medicament tablet toward the housing.

Embodiment 6. The device of embodiment 5, wherein the at least one biasing mechanism includes at least one longitudinal biasing mechanism adapted to bias the medicament tablet by application of pressure along a longitudinal axis of the medicament tablet.

Embodiment 7. The device of embodiment 5 or embodiment 6, wherein the at least one biasing mechanism includes at least one radial biasing mechanism adapted to bias the medicament tablet by application of radial pressure along a perimeter of the medicament tablet.

Embodiment 8. The device of any one of embodiments 1 to 6, wherein the housing of the vibrating ingestible capsule includes an attachment mechanism and the medicament compartment housing includes a corresponding attachment mechanism, for mutual attachment of the vibrating ingestible capsule to the hollow medicament compartment housing.

Embodiment 9. The device of any one of embodiments 1 to 8, wherein the control element is adapted to control a timing or activation delay of the vibration mode of operation such that the vibration mode of operation at least partially transpires within at least one of an estimated absorption time period and an actual absorption time period of the ingestible medicament released from the medicament tablet within the gastrointestinal tract of the user.

Embodiment 10. The device of any one of embodiments 1 to 9, wherein the control element is adapted to activate the vibration agitation mechanism to be operative in the vibration mode of operation in response to receipt of an activation input.

Embodiment 11. The device of embodiment 10, further including at least one sensor adapted to provide the activation input to the control element.

Embodiment 12. The device of embodiment 11, wherein the at least one sensor forms part of the vibrating ingestible capsule.

Embodiment 13. The device of embodiment 11 or embodiment 12, wherein the at least one sensor includes an illumination sensor, adapted to provide an input indicating transition of the device from an illuminated environment to a dark environment.

Embodiment 14. The device of any one of embodiments 11 to 13, wherein the at least one sensor includes a pressure sensor, adapted to provide an input indicating pressure applied to the device, which pressure is indicative of the device moving through a pharynx of the user.

Embodiment 15. The device of any one of embodiments 11 to 14, wherein the at least one sensor includes a temperature sensor, adapted to provide an input indicating transition of the device from an area with ambient temperature to an area with a human body temperature.

Embodiment 16. The device of any one of embodiments 11 to 15, wherein the at least one sensor includes an accelerometer, adapted to provide an input in response to a detected activation motion carried out with the device.

Embodiment 17. The device of any one of embodiments 11 to 16, wherein the at least one sensor includes a moisture sensor, adapted to provide an input indicating transition of the device from a dry environment to a humid environment.

Embodiment 18. The device of any one of embodiments 10 to 14, functionally associated with a control unit remote from the device, and wherein the control element is adapted to receive the activation input from the control unit.

Embodiment 19. The device of any one of embodiments 10 to 18, wherein the control element is adapted to receive the activation input following ingesting of the device.

Embodiment 20. The device of any one of embodiments 10 to 18, wherein the control element is adapted to receive the activation input prior to ingesting of the device.

Embodiment 21. The device of any one of embodiments 10 to 20, wherein the control element is adapted to receive the activation input by receiving a vibration protocol to be used by the control element to control operation of the vibrating agitation mechanism.

Embodiment 22. The device of any one of embodiments 1 to 21, wherein the vibrating agitation mechanism includes at least a radial agitation mechanism adapted, in the vibration mode of operation, to exert radial forces on the housing, in a radial direction with respect to a or the longitudinal axis of the housing, thereby to cause the vibrations exerted by the housing.

Embodiment 23. The device of any one of embodiments 1 to 21, wherein the vibrating agitation mechanism includes at least an axial agitation mechanism adapted, in the vibration mode of operation, to exert axial forces on the housing, in an axial direction with respect to a or the longitudinal axis of the housing, thereby to cause the vibrations exerted by the housing.

Embodiment 24. The device of any one of embodiments 1 to 21, wherein the vibration agitation mechanism includes a radial agitation mechanism adapted, in the vibration mode of operation, to exert radial forces on the housing, in a radial direction with respect to a or the longitudinal axis of the housing, and a separate axial agitation mechanism adapted, in the vibration mode of operation, to exert axial forces on the housing, in an axial direction with respect to a or the longitudinal axis of the housing.

Embodiment 25. The device of any one of embodiments 1 to 21, wherein the vibration agitation mechanism includes a single agitation mechanism adapted, in the vibration mode of operation, to exert radial forces on the housing in a radial direction with respect to a or the longitudinal axis of the housing, and to exert axial forces on the housing, in an axial direction with respect to the longitudinal axis of the housing.

Embodiment 26. The device of any one of embodiments 1 to 25, wherein the control element is adapted to control the vibrating agitation mechanism such that the vibrating mode of operation includes a plurality of cycles, each of the cycles including a vibration duration followed by a repose duration, wherein the housing exerts the vibrations during the vibration duration.

Embodiment 27. The device of embodiment 26, wherein the repose duration is greater than the vibration duration.

Embodiment 28. The device of embodiment 26 or embodiment 27, wherein the vibration duration is in the range of 0.1 second to 10 seconds, 1 second to 10 seconds, 1 second to 9 seconds, 2 seconds to 9 seconds, 3 seconds to 9 seconds, 3 seconds to 8 seconds, 3 seconds to 7 seconds, 3 seconds to 6 seconds, 4 seconds to 6 seconds, or 5 seconds to 6 seconds.

Embodiment 29. The device of any one of embodiments 26 to 28, wherein the repose duration is in the range of 1 second to 180 seconds, 3 seconds to 180 seconds, 5 seconds to 180 seconds, 5 seconds to 150 seconds, 5 seconds to 120 seconds, 8 seconds to 100 seconds, 8 seconds to 30 seconds, 10 seconds to 80 seconds, 10 seconds to 70 seconds, 10 seconds to 60 seconds, 10 seconds to 50 seconds, 10 seconds to 40 seconds, 10 seconds to 30 seconds, 10 seconds to 20 seconds, or 15 seconds to 20 seconds.

Embodiment 30. The device of any one of embodiments 26 to 29, wherein a duration of each of the plurality of cycles is in the range of 1.1 seconds to 200 seconds, 5 seconds to 200 seconds, 10 seconds to 200 seconds, 10 seconds to 150 seconds, 10 seconds to 100 seconds, 10 seconds to 80 seconds, 10 seconds to 50 seconds, 10 seconds to 40 seconds, 10 seconds to 30 seconds, 15 seconds to 50 seconds, 15 seconds to 40 seconds, 15 seconds to 30 seconds, or 15 seconds to 25 seconds.

Embodiment 31. The device of any one of embodiments 1 to 30, wherein the control element is adapted to control the vibrating agitation mechanism such that a cumulative duration of the vibrating mode of operation is in the range of 1 hour to 12 hours, 2 hours to 10 hours, 2 hours to 8 hours, 2 hours to 6 hours, 2 hours to 4 hours, or 2 hours to 3 hours.

Embodiment 32. The device of any one of embodiments 1 to 31, wherein the vibrating agitation mechanism is configured to exert forces on the housing of the vibrating ingestible capsule, such that a net force exerted by the housing on the environment thereof is in the range of 50 grams force (gf) to 600 gf, 50 gf to 550 gf, 100 gf to 550 gf, 100 gf to 500 gf, 150 gf to 500 gf, 200 gf to 500 gf, or 200 gf to 450 gf.

Embodiment 33. The device of any one of embodiments 1 to 32, wherein the vibrating agitation mechanism is configured to exert the forces on the housing to attain a housing vibrational frequency within a range of 10 Hz to 650 Hz, 15 Hz to 600 Hz, 20 Hz to 550 Hz, 30 Hz to 550 Hz, 50 Hz to 500 Hz, 70 Hz to 500 Hz, 100 Hz to 500 Hz, 130 Hz to 500 Hz, or 150 Hz to 500 Hz.

Embodiment 34. The device of any one of embodiments 1 to 33, wherein the medicament compartment housing is at least partially attached to the vibrating ingestible capsule.

Embodiment 35. The device of embodiment 34, wherein the medicament compartment housing is attached to the vibrating ingestible capsule.

Embodiment 36. The device of embodiment 34 or embodiment 35, wherein the medicament compartment housing is fixedly attached to the vibrating ingestible capsule.

Embodiment 37. The device of any one of embodiments 34 to 36, wherein the medicament compartment housing is attached to the vibrating ingestible capsule by snap fit engagement.

Embodiment 38. The device of any one of embodiments 34 to 36, wherein the medicament compartment housing is attached to the vibrating ingestible capsule by threaded engagement.

Embodiment 39. The device of any one of embodiments 34 to 36, wherein the medicament compartment housing is attached to the vibrating ingestible capsule by adhering.

Embodiment 40. The device of any one of embodiments 34 to 36, wherein the medicament compartment housing is attached to the vibrating ingestible capsule by soldering.

Embodiment 41. The device of any one of embodiments 1 to 40, wherein the medicament compartment housing at least partially envelops the vibrating ingestible capsule.

Embodiment 42. The device of embodiment 41, wherein the medicament compartment housing fully envelops the vibrating ingestible capsule.

Embodiment 43. The device of embodiment 42, wherein the medicament compartment housing includes a hollow capsule including the at least one aperture, having the vibrating ingestible capsule disposed therein.

Embodiment 44. The device of any one of embodiments 1 to 43, wherein the hollow of the medicament compartment housing has a volume in the range of 200 mm$^3$ to 800 mm$^3$, 300 mm$^3$ to 700 mm$^3$, or 400 mm$^3$ to 600 mm$^3$.

Embodiment 45. The device of any one of embodiments 1 to 44, wherein the at least one aperture is dimensioned and configured such that the medicament tablet, while whole, cannot be removed from the hollow.

Embodiment 46. The device of any one of embodiments 1 to 44, wherein the at least one aperture is dimensioned and configured to enable insertion of the medicament tablet, via the at least one aperture, into the hollow.

Embodiment 47. The device of any one of embodiments 5 to 46, wherein, in use, the at least one biasing mechanism is adapted to continue biasing the medicament tablet toward the housing, while the ingestible medicament from the medicament tablet is delivered to the environment surrounding the hollow.

Embodiment 48. The device of any one of embodiments 1 to 47, wherein the medicament compartment housing is biodegradable.

Embodiment 49. The device of any one of embodiments 1 to 48, wherein the medicament compartment housing is digestible by the gastrointestinal tract of the user.

Embodiment 50. The device of any one of embodiments 1 to 49, wherein the medicament compartment housing is flexible.

Embodiment 51. The device of any one of embodiments 1 to 50, wherein an exterior contour of at least a portion of the housing is adapted to match an exterior contour of the medicament tablet.

Embodiment 52. The device of embodiment 51, wherein the exterior contour of at least a portion of the housing is concave.

Embodiment 53. The device of any one of embodiments 5 to 52, wherein the at least one biasing mechanism includes at least one pre-loaded compression spring.

Embodiment 54. The device of any one of embodiments 5 to 52, wherein the at least one biasing mechanism includes at least one flexible and resilient leaf.

Embodiment 55. The device of any one of embodiments 1 to 54, further including the medicament tablet including the ingestible medicament.

Embodiment 56. The device of embodiment 55, wherein the medicament tablet has a diameter of up to 5 mm, up to 6 mm, up to 7 mm, up to 8 mm, or up to 9 mm.

Embodiment 57. The device of embodiment 55 or embodiment 56, wherein the medicament tablet has a maximal dimension of up to 10 mm.

Embodiment 58. The device of any one of embodiments 55 to 57, wherein the medicament tablet has a volume of up to 100 mm$^3$, up to 150 mm$^3$, up to 200 mm$^3$, up to 250 mm$^3$, or up to 300 mm$^3$.

Embodiment 59. The device of any one of embodiments 55 to 58, wherein the medicament tablet has a height of up to 3 mm, up to 4 mm, or up to 5 mm.

Embodiment 60. The device of any one of embodiments 55 to 59, wherein the ingestible medicament of the medicament tablet is absorbable in the stomach of the user.

Embodiment 61. The device of any one of embodiments 55 to 60, wherein the ingestible medicament of the medicament tablet is absorbable in the small intestine of the user.

Embodiment 62. The device of any one of embodiments 55 to 61, wherein the ingestible medicament of the medicament tablet is suitable for treatment of one or more symptom or disease, selected from the group consisting of: Parkinsonism; Parkinson's Disease; progressive supranuclear palsy; corticobasal degeneration; multiple system atrophy; Parkinson-plus syndromes; any neurodegenerative disease in which the subject exhibits at least one, at least two, or at least three of the classical features of Parkinson's disease: tremor, postural instability, and akinesia or bradykesia; any neurodegenerative disease in which the subject positively responds to a dopaminergic treatment; any neurodegenerative disease in which the particular subject positively responds to an anticholinergic treatment; Constipation; Crohn's disease; Gastroparesis; irritable bowel syndrome (IBS); diarrhea or loose bowel movements; colitis; Hirschsprung's disease; Dyspepsia; and dysphagia.

Embodiment 63. The device of any one of embodiments 55 to 61, wherein the ingestible medicament of the medicament tablet includes or includes an ingestible medicament selected from the group consisting of: Levodopa; at least one dopaminergic agent; at least one catecholamine precursor; a dopamine precursor; at least one dopamine precursor agent; (L)-3,4-dihydroxyphenylalanine; N-methyl-N-(2-propynyl)-2-methyl-1-phenylethyl-2-amine; tyrosine hydroxylase; apomorphine; at least one anticholinergic agent; at least one agent selected to antagonize at least one cholinergic receptor; benzhexol; orphenadrine; at least one selective allosteric potentiator of metabotropic glutamate receptor 4 (mGluR4); N-phenyl-7-(hydroxylimino)cyclopropa[b]chromen-1a-carboxamide; at least one osmotic agent; magnesium citrate; magnesium hydroxide; polyethylene glycol; sodium phosphate; MiraLAX®; at least one contraction stimulating agent; bisacodyl; senna; Correctol; Ducodyl; Dulcolax; Senexon; Senokot; at least one stool softening agent; docusate sodium; Colace; Linaclotide; Lactulose; Lubiprostone; Plecanatide; Prucaltride; Loperamide; and bismuth subsalicylate.

Embodiment 64. A method of delivering an ingestible medicament into a gastrointestinal tract of a user, the method including:

providing to the user the device according to any one of embodiments 55 to 63, for ingestion by the user;

following the user ingesting the device, controlling the vibrating ingestible capsule such that the vibration mode of operation at least partially transpires within at least one of an estimated absorption time period and an actual absorption time period of the ingestible medicament within the gastrointestinal tract of the user.

Embodiment 65. A method of delivering an ingestible medicament into a gastrointestinal tract of a user, the method including:

providing to the user the device according to any one of embodiments 1 to 54;

inserting into the hollow of the medicament compartment housing the medicament tablet; and following the user ingesting the device having the medicament tablet disposed in the hollow, controlling the vibrating ingestible capsule such that the vibration mode of operation at least partially transpires within at least one of an estimated absorption time period and an actual absorption time period of the ingestible medicament within the gastrointestinal tract of the user.

Embodiment 66. A hollow medicament delivery compartment adapted to be associated with a vibrating ingestible capsule for delivery of an ingestible medicament of a medicament tablet into the gastrointestinal tract of a user, the hollow medicament delivery compartment being dimensioned and configured to have the medicament tablet disposed therein, and including at least one aperture formed in the hollow medicament delivery compartment, wherein the at least one aperture is dimensioned and configured to enable fluid communication between an environment surrounding the hollow medicament delivery compartment.

Embodiment 67. The hollow medicament delivery compartment of embodiment 66, wherein the at least one aperture is dimensioned and configured such that, when the medicament tablet is disposed within the hollow and the hollow medicament delivery compartment is in the gastrointestinal tract of the user, the ingestible medicament of the medicament tablet enters the environment surrounding the hollow medicament delivery compartment for delivery thereof to the body of the user.

Embodiment 68. The hollow medicament delivery compartment of any one of embodiments 66 to 67, further including at least one biasing mechanism adapted, when the medicament tablet is disposed within the hollow of the hollow medicament delivery compartment, to bias the medicament tablet toward the vibrating ingestible capsule.

Embodiment 69. The hollow medicament delivery compartment of embodiment 68, wherein the at least one biasing mechanism includes at least one longitudinal biasing mechanism adapted to bias the medicament tablet by application of pressure along a longitudinal axis of the medicament tablet.

Embodiment 70. The hollow medicament delivery compartment of embodiment 68 or embodiment 69, wherein the at least one biasing mechanism includes at least one radial biasing mechanism adapted to bias the medicament tablet by application of radial pressure along a perimeter of the medicament tablet.

Embodiment 71. The hollow medicament delivery compartment of any one of embodiments 66 to 70, wherein the hollow medicament delivery compartment includes an attachment mechanism for mutual attachment to a corresponding attachment mechanism of the vibrating ingestible capsule.

Embodiment 72. The hollow medicament delivery compartment of any one of embodiments 66 to 71, wherein the hollow medicament delivery compartment is adapted to be at least partially attached to the vibrating ingestible capsule.

Embodiment 73. The hollow medicament delivery compartment of embodiment 72, wherein the hollow medicament delivery compartment is adapted to be attached to the vibrating ingestible capsule.

Embodiment 74. The hollow medicament delivery compartment of embodiment 72 or embodiment 73, wherein the hollow medicament delivery compartment is adapted to be fixedly attached to the vibrating ingestible capsule.

Embodiment 75. The hollow medicament delivery compartment of any one of embodiments 72 to 74, wherein the hollow medicament delivery compartment is adapted to be attached to the vibrating ingestible capsule by snap fit engagement.

Embodiment 76. The hollow medicament delivery compartment of any one of embodiments 72 to 74, wherein the hollow medicament delivery compartment is adapted to be attached to the vibrating ingestible capsule by threaded engagement.

Embodiment 77. The hollow medicament delivery compartment of any one of embodiments 72 to 74, wherein the hollow medicament delivery compartment is adapted to be attached to the vibrating ingestible capsule by adhering.

Embodiment 78. The hollow medicament delivery compartment of any one of embodiments 72 to 74, wherein the hollow medicament delivery compartment is adapted to be attached to the vibrating ingestible capsule by soldering.

Embodiment 79. The hollow medicament delivery compartment of any one of embodiments 66 to 78, wherein the hollow medicament delivery compartment is adapted to at least partially envelop the vibrating ingestible capsule.

Embodiment 80. The hollow medicament delivery compartment of embodiment 79, wherein the hollow medicament delivery compartment is adapted to fully envelop the vibrating ingestible capsule.

Embodiment 81. The hollow medicament delivery compartment of embodiment 80, wherein the hollow medicament delivery compartment includes a hollow capsule including the at least one aperture, having the vibrating ingestible capsule disposed therein.

Embodiment 82. The hollow medicament delivery compartment of any one of embodiments 66 to 81, wherein the hollow medicament delivery compartment has a volume in the range of 200 mm$^3$ to 800 mm$^3$, 300 mm$^3$ to 700 mm$^3$, 400 mm$^3$ to 600 mm$^3$, or 500 mm$^3$.

Embodiment 83. The hollow medicament delivery compartment of any one of embodiments 66 to 82, wherein the at least one aperture is dimensioned and configured such that when the hollow medicament delivery compartment is attached to the vibrating ingestible capsule, the medicament tablet, while whole, cannot be removed from the hollow medicament delivery compartment.

Embodiment 84. The hollow medicament delivery compartment of any one of embodiments 66 to 82, wherein the at least one aperture is dimensioned and configured to enable insertion of the medicament tablet, via the at least one aperture, into the hollow medicament delivery compartment.

Embodiment 85. The hollow medicament delivery compartment of any one of embodiments 68 to 84, wherein, in use within the gastrointestinal tract of the user, the biasing mechanism is adapted to continue biasing the medicament tablet toward the ingestible vibrating capsule, while the ingestible medicament from the medicament tablet is delivered to the environment surrounding the hollow medicament delivery compartment.

Embodiment 86. The hollow medicament delivery compartment of any one of embodiments 66 to 85, wherein the hollow medicament delivery compartment is biodegradable.

Embodiment 87. The hollow medicament delivery compartment of any one of embodiments 66 to 86, wherein the hollow medicament delivery compartment is digestible by the gastrointestinal tract of the user.

Embodiment 88. The hollow medicament delivery compartment of any one of embodiments 66 to 87, wherein the hollow medicament delivery compartment is flexible.

Embodiment 89. The hollow medicament delivery compartment of any one of embodiments 68 to 88, wherein the at least one biasing mechanism includes at least one pre-loaded compression spring.

Embodiment 90. The hollow medicament delivery compartment of any one of embodiments 68 to 89, wherein the at least one biasing mechanism includes at least one flexible and resilient leaf.

Embodiment 91. The hollow medicament delivery compartment of any one of embodiments 66 to 90, further including the medicament tablet including the medicament disposed within the hollow medicament delivery compartment.

Embodiment 92. The hollow medicament delivery compartment of embodiment 91, wherein the medicament tablet has a diameter of up to 5 mm, up to 6 mm, up to 7 mm, up to 8 mm, or up to 9 mm.

Embodiment 93. The hollow medicament delivery compartment of embodiment 91 or embodiment 92, wherein the medicament tablet has a maximal dimension of up to 10 mm.

Embodiment 94. The hollow medicament delivery compartment of any one of embodiments 91 to 93, wherein the medicament tablet has a volume of 100 mm$^3$, up to 150 mm$^3$, up to 200 mm$^3$, up to 250 mm$^3$, or up to 300 mm$^3$.

Embodiment 95. The hollow medicament delivery compartment of any one of embodiments 91 to 94, wherein the medicament tablet has a height of up to 3 mm, up to 4 mm, or up to 5 mm.

Embodiment 96. The hollow medicament delivery compartment of any one of embodiments 91 to 95, wherein the ingestible medicament of the medicament tablet is absorbable in the stomach of the user.

Embodiment 97. The hollow medicament delivery compartment of any one of embodiments 91 to 96, wherein the ingestible medicament of the medicament tablet is absorbable in the small intestine of the user.

Embodiment 98. The hollow medicament delivery compartment of any one of embodiments 91 to 97, wherein the ingestible medicament of the medicament tablet is suitable for treatment of one or more symptom or disease, selected from the group listed in embodiment 62.

Embodiment 99. The hollow medicament delivery compartment of any one of embodiments 91 to 98, wherein the ingestible medicament of the medicament tablet includes or includes an ingestible medicament selected from the group listed in embodiment 63.

Embodiment 100. A vibrating ingestible capsule adapted to be associated with a hollow medicament delivery compartment for delivering an ingestible medicament of a medicament tablet into the gastrointestinal tract of a user, the vibrating ingestible capsule including:

a housing including an attachment mechanism adapted for mutual attachment to a corresponding attachment mechanism of the hollow medicament delivery compartment;

a vibrating agitation mechanism disposed within the housing and adapted such that, in a vibration mode of operation, the housing exerts vibrations on an environment surrounding the vibrating gastrointestinal capsule;

a power supply disposed within the housing and adapted to power the vibrating agitation mechanism; and a control element adapted to activate the vibrating agitation mechanism to be operative in the vibration mode of operation, wherein at least one vibration parameter of the vibrating agitation mechanism is set so as to promote absorption of the ingestible medicament into the bloodstream of the user.

Embodiment 101. The vibrating ingestible capsule of embodiment 100, wherein the at least one vibration parameter includes at least one of a vibration frequency, a cumulative vibration duration, a number of vibration cycles per time unit, a duration of a vibration duration within a vibration cycle, a duration of a repose duration within a vibration cycle, a total duration of a single vibration cycle, and a net force exerted by the housing on the environment.

Embodiment 102. The vibrating ingestible capsule of any one of embodiments 100 to 101, wherein the control element is adapted to control a timing or activation delay of the vibration mode of operation such that the vibration mode of operation at least partially transpires within at least one of an estimated absorption time period and an actual absorption time period of medicament released from the medicament tablet within the gastrointestinal tract of the user.

Embodiment 103. The vibrating ingestible capsule of any one of embodiments 100 to 102, wherein the control element is adapted to activate the vibration agitation mechanism to be operative in the vibration mode of operation in response to receipt of an activation input.

Embodiment 104. The vibrating ingestible capsule of embodiment 103, further including at least one sensor adapted to provide the activation input to the control element.

Embodiment 105. The vibrating ingestible capsule of embodiment 104, wherein the at least one sensor forms part of the vibrating ingestible capsule.

Embodiment 106. The vibrating ingestible capsule of embodiment 104 or embodiment 105, wherein the at least one sensor includes an illumination sensor, adapted to provide an input indicating transition of the vibrating ingestible capsule from an illuminated environment to a dark environment.

Embodiment 107. The vibrating ingestible capsule of any one of embodiments 104 to 106, wherein the at least one sensor includes a pressure sensor, adapted to provide an input indicating pressure applied to the vibrating ingestible capsule, which pressure is indicative of the vibrating ingestible capsule moving through a pharynx of the user.

Embodiment 108. The vibrating ingestible capsule of any one of embodiments 104 to 107, wherein the at least one sensor includes a temperature sensor, adapted to provide an input indicating transition of the vibrating ingestible capsule from an area with ambient temperature to an area with a human body temperature.

Embodiment 109. The vibrating ingestible capsule of any one of embodiments 104 to 108, wherein the at least one sensor includes an accelerometer, adapted to provide an input in response to a detected activation motion carried out with the vibrating ingestible capsule.

Embodiment 110. The vibrating ingestible capsule of any one of embodiments 104 to 109, wherein the at least one sensor includes a moisture sensor, adapted to provide an input indicating transition of the vibrating ingestible capsule from a dry environment to a humid environment.

Embodiment 111. The vibrating ingestible capsule of any one of embodiments 103 to 110, functionally associated with a control unit remote from the vibrating ingestible capsule, and wherein the control element is adapted to receive the activation input from the control unit.

Embodiment 112. The vibrating ingestible capsule of any one of embodiments 103 to 111, wherein the control element is adapted to receive the activation input following ingesting of the vibrating ingestible capsule.

Embodiment 113. The vibrating ingestible capsule of any one of embodiments 103 to 111, wherein the control element is adapted to receive the activation input prior to ingesting of the vibrating ingestible capsule.

Embodiment 114. The vibrating ingestible capsule of any one of embodiments 103 to 113, wherein the control element is adapted to receive the activation input by receiving a vibration protocol to be used by the control element to control operation of the vibrating agitation mechanism.

Embodiment 115. The vibrating ingestible capsule of any one of embodiments 100 to 114, wherein the vibrating agitation mechanism includes at least a radial agitation mechanism adapted, in the vibration mode of operation, to exert radial forces on the housing, in a radial direction with respect to a or the longitudinal axis of the housing, thereby to cause the vibrations exerted by the housing.

Embodiment 116. The vibrating ingestible capsule of any one of embodiments 100 to 114, wherein the vibrating agitation mechanism includes at least an axial agitation mechanism adapted, in the vibration mode of operation, to exert axial forces on the housing, in an axial direction with respect to a or the longitudinal axis of the housing, thereby to cause the vibrations exerted by the housing.

Embodiment 117. The vibrating ingestible capsule of any one of embodiments 100 to 114, wherein the vibration agitation mechanism includes a radial agitation mechanism adapted, in the vibration mode of operation, to exert radial forces on the housing, in a radial direction with respect to a or the longitudinal axis of the housing, and a separate axial agitation mechanism adapted, in the vibration mode of operation, to exert axial forces on the housing, in an axial direction with respect to a or the longitudinal axis of the housing.

Embodiment 118. The vibrating ingestible capsule of any one of embodiments 100 to 114, wherein the vibration agitation mechanism includes a single agitation mechanism adapted, in the vibration mode of operation, to exert radial forces on the housing in a radial direction with respect to a or the longitudinal axis of the housing, and to exert axial forces on the housing, in an axial direction with respect to the longitudinal axis of the housing.

Embodiment 119. The vibrating ingestible capsule of any one of embodiments 100 to 118, wherein the control element is adapted to control the vibrating agitation mechanism such that the vibrating mode of operation includes a plurality of cycles, each of the cycles including a vibration duration followed by a repose duration, wherein the housing exerts the vibrations during the vibration duration.

Embodiment 120. The vibrating ingestible capsule of embodiment 119, wherein the repose duration is greater than the vibration duration.

Embodiment 121. The vibrating ingestible capsule of embodiment 119 or embodiment 120, wherein the vibration duration is in the range of 0.1 second to 10 seconds, 1 second to 10 seconds, 1 second to 9 seconds, 2 seconds to 9 seconds, 3 seconds to 9 seconds, 3 seconds to 8 seconds, 3 seconds to 7 seconds, 3 seconds to 6 seconds, 4 seconds to 6 seconds, or 5 seconds to 6 seconds.

Embodiment 122. The vibrating ingestible capsule of any one of embodiments 119 to 121, wherein the repose duration is in the range of 1 second to 180 seconds, 3 seconds to 180 seconds, 5 seconds to 180 seconds, 5 seconds to 150 seconds, 5 seconds to 120 seconds, 8 seconds to 100 seconds, 8 seconds to 30 seconds, 10 seconds to 80 seconds, 10 seconds to 70 seconds, 10 seconds to 60 seconds, 10 seconds to 50 seconds, 10 seconds to 40 seconds, 10 seconds to 30 seconds, 10 seconds to 20 seconds, or 15 seconds to 20 seconds.

Embodiment 123. The vibrating ingestible capsule of any one of embodiments 119 to 122, wherein a duration of each of the plurality of cycles is in the range of 1.1 seconds to 200 seconds, 5 seconds to 200 seconds, 10 seconds to 200 seconds, 10 seconds to 150 seconds, 10 seconds to 100 seconds, 10 seconds to 80 seconds, 10 seconds to 50 seconds, 10 seconds to 40 seconds, 10 seconds to 30 seconds, 15 seconds to 50 seconds, 15 seconds to 40 seconds, 15 seconds to 30 seconds, or 15 seconds to 25 seconds.

Embodiment 124. The vibrating ingestible capsule of any one of embodiments 100 to 123, wherein the control element is adapted to control the vibrating agitation mechanism such that a cumulative duration of the vibrating mode of operation is in the range of 1 hour to 12 hours, 2 hours to 10 hours, 2 hours to 8 hours, 2 hours to 6 hours, 2 hours to 4 hours, or 2 hours to 3 hours.

Embodiment 125. The vibrating ingestible capsule of any one of embodiments 100 to 124, wherein the vibrating agitation mechanism is configured to exert forces on the housing of the vibrating ingestible capsule, such that a net force exerted by the housing on the environment thereof is in the range of 50 grams force (gf) to 600 gf, 50 gf to 550 gf, 100 gf to 550 gf, 100 gf to 500 gf, 150 gf to 500 gf, 200 gf to 500 gf, or 200 gf to 450 gf.

Embodiment 126. The vibrating ingestible capsule of any one of embodiments 100 to 125, wherein the vibrating agitation mechanism is configured to exert the forces on the housing to attain a housing vibrational frequency within a range of 10 Hz to 650 Hz, 15 Hz to 600 Hz, 20 Hz to 550 Hz, 30 Hz to 550 Hz, 50 Hz to 500 Hz, 70 Hz to 500 Hz, 100 Hz to 500 Hz, 130 Hz to 500 Hz, or 150 Hz to 500 Hz.

Embodiment 127. The vibrating ingestible capsule of any one of embodiments 100 to 126, wherein the housing is adapted to be at least partially attached to the hollow medicament delivery compartment.

Embodiment 128. The vibrating ingestible capsule of embodiment 127, wherein the housing is adapted to be attached to the hollow medicament delivery compartment.

Embodiment 129. The vibrating ingestible capsule of embodiment 127 or embodiment 128, wherein the housing is adapted to be fixedly attached to the hollow medicament delivery compartment.

Embodiment 130. The vibrating ingestible capsule of any one of embodiments 127 to 129, the housing is adapted to be attached to the hollow medicament delivery compartment by snap fit engagement.

Embodiment 131. The vibrating ingestible capsule of any one of embodiments 127 to 129, the housing is adapted to be attached to the hollow medicament delivery compartment by threaded engagement.

Embodiment 132. The vibrating ingestible capsule of any one of embodiments 127 to 129, the housing is adapted to be attached to the hollow medicament delivery compartment by adhering.

Embodiment 133. The vibrating ingestible capsule of any one of embodiments 127 to 129, the housing is adapted to be attached to the hollow medicament delivery compartment by soldering.

Embodiment 134. The vibrating ingestible capsule of any one of embodiments 100 to 127, the wherein the housing is adapted to be at least partially enveloped by the hollow medicament delivery compartment.

Embodiment 135. The vibrating ingestible capsule of embodiment 134, wherein the housing is adapted to be fully enveloped by the hollow medicament delivery compartment.

Embodiment 136. A method for delivering an ingestible medicament of a medicament tablet into the gastrointestinal tract of a user, the method including:
  providing a vibrating ingestible capsule including:
    a housing;
    a vibrating agitation mechanism disposed within the housing and adapted such that, in a vibration mode of operation, the housing exerts vibrations on an environment surrounding the vibrating gastrointestinal capsule;
    a power supply disposed within the housing and adapted to power the vibrating agitation mechanism; and
    a control element adapted to activate the vibrating agitation mechanism to be operative in the vibration mode of operation; and
  associating a hollow medicament compartment housing with the housing, the hollow medicament compartment having at least one aperture formed therein;
  inserting the medicament tablet into the hollow medicament compartment housing;
  ingesting an assembly of the vibrating ingestible capsule, the hollow medicament compartment housing, and the medicament tablet by the user; and
  following the user ingesting the assembly, controlling the vibrating ingestible capsule such that the vibration mode of operation at least partially transpires within at least one of an estimated absorption time period and an actual absorption time period of the ingestible medicament within the gastrointestinal tract of the user.

Embodiment 137. The method of embodiment 136, wherein the controlling the vibrating ingestible capsule includes setting at least one vibration parameter of the vibrating ingestible capsule so as to promote absorption of the ingestible medicament into the bloodstream of the user.

Embodiment 138. The method of embodiment 137, wherein the setting the at least one vibration parameter includes setting at least one of a vibration frequency, a cumulative vibration duration, a number of vibration cycles per time unit, a duration of a vibration duration within a vibration cycle, a duration of a repose duration within a vibration cycle, a total duration of a single vibration cycle, and a net force exerted by the housing on the environment.

Embodiment 139. The method of any one of embodiments 136 to 138, further including, following the inserting the medicament tablet, biasing the medicament tablet toward the housing of the vibrating ingestible capsule.

Embodiment 140. The method of embodiment 139, wherein the biasing includes biasing the medicament tablet by application of pressure along a longitudinal axis of the medicament tablet.

Embodiment 141. The method of embodiment 139 or embodiment 140, wherein the biasing includes biasing the medicament tablet by application of radial pressure along a perimeter of the medicament tablet.

Embodiment 142. The method of any one of embodiments 136 to 141, wherein the housing of the vibrating ingestible capsule includes an attachment mechanism, the hollow medicament compartment housing includes a corresponding attachment mechanism, and the associating includes mutually attaching the vibrating ingestible capsule to the hollow medicament compartment housing.

Embodiment 143. The method of any one of embodiments 136 to 142, wherein the controlling includes controlling a timing or activation delay of the vibration mode of operation such that the vibration mode of operation at least partially transpires within at least one of an estimated absorption time period and an actual absorption time period of an ingestible medicament released from the medicament tablet within the gastrointestinal tract of the user.

Embodiment 144. The method of any one of embodiments 136 to 143, further including, prior to the controlling, at the control element receiving an activation input, and
  wherein the controlling includes activating the vibration agitation mechanism to be operative in the vibration mode of operation following the receiving the activation input.

Embodiment 145. The method of embodiment 144, wherein the receiving the activation input includes receiving the activation input from at least one sensor.

Embodiment 146. The method of embodiment 145, wherein the receiving the activation input includes receiving, from an illumination sensor, an input indicating transition of the assembly from an illuminated environment to a dark environment.

Embodiment 147. The method of any one of embodiments 145 to 146, wherein the receiving the activation input includes receiving, from a pressure sensor, an input indicating pressure applied to the assembly, which pressure is indicative of the assembly moving through a pharynx of the user.

Embodiment 148. The method of any one of embodiments 145 to 147, wherein the receiving the activation input includes receiving, from a temperature sensor, an input indicating transition of the assembly from an area with ambient temperature to an area with a human body temperature.

Embodiment 149. The method of any one of embodiments 145 to 148, wherein the receiving the activation input includes receiving, from an accelerometer, an input in response to a detected activation motion carried out with the assembly.

Embodiment 150. The method of any one of embodiments 145 to 149, wherein the receiving the activation input includes receiving, from a moisture sensor, an input indicating transition of the assembly from a dry environment to a humid environment.

Embodiment 151. The method of any one of embodiments 144 to 150, wherein the receiving the activation input includes receiving the activation input from a control unit remote from the assembly and functionally associated with the control element.

Embodiment 152. The method of any one of embodiments 144 to 151, wherein the receiving the activation input occurs following the ingesting of the assembly.

Embodiment 153. The method of any one of embodiments 144 to 152, wherein the receiving the activation input occurs prior to the ingesting of the assembly.

Embodiment 154. The method of any one of embodiments 144 to 153, wherein the receiving the activation input includes receiving a vibration protocol to be used by the control element for the controlling operation of the vibrating agitation mechanism.

Embodiment 155. The method of any one of embodiments 136 to 154, wherein the controlling the vibrating agitation mechanism includes controlling the vibration agitation mechanism such that the vibrating mode of operation includes a plurality of cycles, each of the cycles including a vibration duration followed by a repose duration, wherein the housing exerts the vibrations during the vibration duration.

Embodiment 156. The method of embodiment 155, wherein the repose duration is greater than the vibration duration.

Embodiment 157. The method of embodiment 155 or embodiment 156, wherein the vibration duration is in the range of 0.1 second to 10 seconds, 1 second to 10 seconds, 1 second to 9 seconds, 2 seconds to 9 seconds, 3 seconds to 9 seconds, 3 seconds to 8 seconds, 3 seconds to 7 seconds, 3 seconds to 6 seconds, 4 seconds to 6 seconds, or 5 seconds to 6 seconds.

Embodiment 158. The method of any one of embodiments 155 to 157, wherein the repose duration is in the range of 1 second to 180 seconds, 3 seconds to 180 seconds, 5 seconds to 180 seconds, 5 seconds to 150 seconds, 5 seconds to 120 seconds, 8 seconds to 100 seconds, 8 seconds to 30 seconds, 10 seconds to 80 seconds, 10 seconds to 70 seconds, 10 seconds to 60 seconds, 10 seconds to 50 seconds, 10 seconds to 40 seconds, 10 seconds to 30 seconds, 10 seconds to 20 seconds, or 15 seconds to 20 seconds.

Embodiment 159. The method of any one of embodiments 155 to 158, wherein a duration of each of the plurality of cycles is in the range of 1.1 seconds to 200 seconds, 5 seconds to 200 seconds, 10 seconds to 200 seconds, 10 seconds to 150 seconds, 10 seconds to 100 seconds, 10 seconds to 80 seconds, 10 seconds to 50 seconds, 10 seconds to 40 seconds, 10 seconds to 30 seconds, 15 seconds to 50 seconds, 15 seconds to 40 seconds, 15 seconds to 30 seconds, or 15 seconds to 25 seconds.

Embodiment 160. The method of any one of embodiments 136 to 159, wherein the controlling includes controlling the vibrating agitation mechanism such that a cumulative duration of the vibrating mode of operation is in the range of 1 hour to 12 hours, 2 hours to 10 hours, 2 hours to 8 hours, 2 hours to 6 hours, 2 hours to 4 hours, or 2 hours to 3 hours.

Embodiment 161. The method of any one of embodiments 136 to 160, wherein the controlling including controlling the vibrating agitation mechanism to exert forces on the housing of the vibrating ingestible capsule, such that a net force exerted by the housing on the environment thereof is in the range of 50 grams force (gf) to 600 gf, 50 gf to 550 gf, 100 gf to 550 gf, 100 gf to 500 gf, 150 gf to 500 gf, 200 gf to 500 gf, or 200 gf to 450 gf.

Embodiment 162. The method of any one of embodiments 136 to 161, wherein the controlling including controlling the vibrating agitation mechanism to exert the forces on the housing to attain a housing vibrational frequency within a range of 10 Hz to 650 Hz, 15 Hz to 600 Hz, 20 Hz to 550 Hz, 30 Hz to 550 Hz, 50 Hz to 500 Hz, 70 Hz to 500 Hz, 100 Hz to 500 Hz, 130 Hz to 500 Hz, or 150 Hz to 500 Hz.

Embodiment 163. The method of any one of embodiments 136 to 162, wherein the associating includes at least partially attaching the medicament compartment housing to the vibrating ingestible capsule.

Embodiment 164. The method of embodiment 163, wherein the associating includes attaching the medicament compartment housing to the vibrating ingestible capsule.

Embodiment 165. The method of embodiment 163 or embodiment 164, wherein the associating includes fixedly attaching the medicament compartment housing to the vibrating ingestible capsule.

Embodiment 166. The method of any one of embodiments 163 to 165, wherein the associating includes attaching the medicament compartment housing to the vibrating ingestible capsule by snap fit engagement.

Embodiment 167. The method of any one of embodiments 163 to 165, wherein the associating includes attaching the medicament compartment housing to the vibrating ingestible capsule by threaded engagement.

Embodiment 168. The method of any one of embodiments 163 to 165, wherein the associating includes attaching the medicament compartment housing to the vibrating ingestible capsule by adhering.

Embodiment 169. The method of any one of embodiments 163 to 165, wherein the associating includes attaching the medicament compartment housing to the vibrating ingestible capsule by soldering.

Embodiment 170. The method of any one of embodiments 136 to 162, wherein the associating includes at least partially enveloping the medicament compartment housing around the vibrating ingestible capsule.

Embodiment 171. The method of embodiment 170, wherein the associating includes fully enveloping the medicament compartment housing around the vibrating ingestible capsule.

Embodiment 172. The method of any one of embodiments 136 to 171, wherein the inserting including inserting the medicament tablet, via the at least one aperture, into the hollow medicament compartment housing.

Embodiment 173. The method of any one of embodiments 136 to 172, wherein the medicament tablet has a diameter of up to 5 mm, up to 6 mm, up to 7 mm, up to 8 mm, or up to 9 mm.

Embodiment 174. The method of any one of embodiments 136 to 173, wherein the medicament tablet has a maximal dimension of up to 10 mm.

Embodiment 175. The method of any one of embodiments 136 to 174, wherein the medicament tablet has a volume of up to 100 $mm^3$, up to 150 $mm^3$, up to 200 $mm^3$, up to 250 $mm^3$, or up to 300 $mm^3$.

Embodiment 176. The method of any one of embodiments 136 to 175, wherein the medicament tablet has a height of up to 3 mm, up to 4 mm, or up to 5 mm.

Embodiment 177. The method of any one of embodiments 136 to 176, wherein the ingestible medicament of the medicament tablet is absorbable in the stomach of the user.

Embodiment 178. The method of any one of embodiments 136 to 177, wherein the medicament tablet includes an ingestible medicament absorbable in the small intestine of the user.

Embodiment 179. The method of any one of embodiments 136 to 178, the ingestible medicament of the medicament tablet is suitable for treatment of one or more symptom or disease, selected from the group listed in embodiment 62.

Embodiment 180. The method of any one of embodiments 136 to 179, wherein the ingestible medicament of the medicament tablet includes or includes an ingestible medicament selected from the group listed in embodiment 63.

It will be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A hollow medicament delivery compartment adapted to be associated with a vibrating ingestible capsule for delivery of an ingestible medicament of a medicament tablet into the gastrointestinal tract of a user, the hollow medicament delivery compartment comprising:
   a hollow medicament compartment housing, adapted to be associated with the vibrating ingestible capsule and defining a hollow dimensioned and configured to have the medicament tablet disposed therein;
   at least one aperture formed in said hollow medicament compartment housing; and
   radial biasing mechanism adapted, when the medicament tablet is disposed within said hollow of said medicament compartment housing, to bias said medicament tablet to be centered along a longitudinal axis of the hollow medicament compartment housing by application of radial pressure along a perimeter of the medicament tablet,
   wherein said at least one aperture is dimensioned and configured to enable fluid communication between an environment surrounding said hollow medicament delivery compartment and said hollow,
   wherein said at least one aperture is dimensioned and configured such that, when the medicament tablet is disposed within said hollow and said hollow medicament delivery compartment is in the gastrointestinal tract of the user, the ingestible medicament of the medicament tablet enters said environment surrounding said hollow medicament delivery compartment for delivery of the ingestible medicament to the body of the user.

2. The hollow medicament delivery compartment of claim 1, further comprising a longitudinal biasing mechanism anchored to the hollow medicament compartment housing and adapted to bias the medicament tablet toward a surface of the hollow medicament compartment housing, which surface is adapted to engage the vibrating ingestible capsule, by application of pressure along a longitudinal axis of the medicament tablet.

3. The hollow medicament delivery compartment of claim 2, wherein said at least one longitudinal biasing mechanism is adapted, when the medicament tablet is disposed within said hollow, to constantly and continuously bias the medicament tablet toward the surface of said hollow medicament compartment housing.

4. The hollow medicament delivery compartment of claim 1, wherein said hollow medicament compartment housing is adapted to be at least partially attached to the vibrating ingestible capsule.

5. The hollow medicament delivery compartment of claim 1, wherein said hollow medicament compartment housing is adapted to at least partially envelop the vibrating ingestible capsule.

6. The hollow medicament delivery compartment of claim 5, wherein said hollow medicament compartment housing comprises a hollow capsule including said at least one aperture, said hollow capsule adapted to have said vibrating ingestible capsule disposed therein.

7. The hollow medicament delivery compartment of claim 1, wherein said at least one aperture is dimensioned and configured such that said medicament tablet, while whole, cannot be removed from said hollow.

8. The hollow medicament delivery compartment of claim 1, wherein said medicament compartment housing is biodegradable.

9. The hollow medicament delivery compartment of claim 1, further comprising said medicament tablet including said ingestible medicament.

10. The hollow medicament delivery compartment of claim 9, wherein said ingestible medicament of said medicament tablet is absorbable in at least one of the stomach of the user and the small intestine of the user.

11. The hollow medicament delivery compartment of claim 1, wherein the hollow medicament delivery compartment is devoid of a vibrating mechanism.

12. The hollow medicament delivery compartment of claim 1, wherein said medicament compartment housing is digestible by the gastrointestinal tract of the user.

13. The hollow medicament delivery compartment of claim 1, wherein said medicament compartment housing is flexible.

14. A method for delivering an ingestible medicament of a medicament tablet into the gastrointestinal tract of a user, the method including:
   obtaining a vibrating ingestible capsule including:
      a capsule housing;
      a vibrating agitation mechanism disposed within the housing and adapted such that, in a vibration mode of operation, the capsule housing exerts vibrations on an environment surrounding the vibrating gastrointestinal capsule;
      a power supply disposed within the housing and adapted to power the vibrating agitation mechanism; and a control element adapted to activate the vibrating agitation mechanism to be operative in the vibration mode of operation, such that the vibration mode of operation at least partially transpires within at least one of an estimated absorption time period and an actual absorption time period of the ingestible medicament within the gastrointestinal tract of the user; and associating a hollow medicament delivery compartment of claim 1 with the capsule housing.

15. The method of claim 14, further comprising inserting the medicament tablet into the hollow of said hollow medicament delivery compartment.

16. The method of claim 14, further comprising, following said inserting of the medicament tablet, biasing the medicament tablet toward said capsule housing.

17. The method of claim 14, wherein the associating comprises at least partially attaching said hollow medicament compartment housing to said capsule housing.

18. The method of claim 14, wherein the associating comprises at least partially enveloping said hollow medicament compartment housing around the vibrating ingestible capsule.

19. The method of claim 14, wherein the inserting comprises inserting the medicament tablet, via said at least one aperture, into said hollow medicament compartment housing.

* * * * *